United States Patent
Saitou et al.

(10) Patent No.: US 8,673,128 B2
(45) Date of Patent: Mar. 18, 2014

(54) GAS SENSOR ELEMENT, GAS SENSOR, AND PRODUCTION METHOD THEREOF

(71) Applicant: Denso Corporation, Kariya (JP)

(72) Inventors: Masami Saitou, Nagoya (JP); Namitsugu Fujii, Yokkaichi (JP); Norikazu Kajiyama, Chiryu (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 13/628,242

(22) Filed: Sep. 27, 2012

(65) Prior Publication Data

US 2013/0075256 A1  Mar. 28, 2013

(30) Foreign Application Priority Data

Sep. 27, 2011 (JP) .................. 2011-210167

(51) Int. Cl.
*G01N 27/407* (2006.01)
(52) U.S. Cl.
USPC ........... 204/424; 204/425; 204/426; 204/427; 204/428; 204/429; 73/23.31; 73/23.32
(58) Field of Classification Search
USPC .................. 204/424–429; 73/23.31–23.32
See application file for complete search history.

(56) References Cited

U.S. PATENT DOCUMENTS

| | | | |
|---|---|---|---|
| 4,208,265 A | 6/1980 | Hori et al. | |
| 4,908,119 A | 3/1990 | Saito et al. | |
| 4,980,042 A * | 12/1990 | Shiomi et al. | 204/427 |
| 6,346,178 B1 * | 2/2002 | Lankheet | 204/424 |
| 2002/0063059 A1 | 5/2002 | Sugiyama et al. | |
| 2004/0118703 A1 * | 6/2004 | Wang et al. | 205/780.5 |
| 2006/0219554 A1 | 10/2006 | Mori et al. | |

FOREIGN PATENT DOCUMENTS

| | | |
|---|---|---|
| JP | A-S63-061160 | 3/1988 |
| JP | 06-048258 | 6/1994 |
| JP | 2002-228626 | 8/2002 |
| JP | 2006-308545 | 11/2006 |
| JP | 2007-278941 | 10/2007 |
| JP | 01-253649 | 10/2009 |
| JP | A2010-145214 | 7/2010 |

OTHER PUBLICATIONS

United States Office Action issued for U.S. Appl. No. 13/767,326, dated Mar. 28, 2013.
Japanese Notification of Reasons for Rejection issued for Japanese Patent Application No. 2011-210167 dated Aug. 20, 2013 (with partial English translation).

* cited by examiner

*Primary Examiner* — Keith Hendricks
*Assistant Examiner* — Bach Dinh
(74) *Attorney, Agent, or Firm* — Nixon & Vanderhye P.C.

(57) ABSTRACT

A gas sensor element includes an insulating ceramic base, a solid electrolyte body, and a heating element. The solid electrolyte body is disposed in an opening of the insulating ceramic base and has a measuring electrode affixed to one of major surfaces thereof and a reference electrode affixed to the other major surface. The measuring electrode is exposed to gas to be measured. The reference electrode is exposed to a reference gas. The heating element works to activate the solid electrolyte body and is mounted on one of opposed surfaces of the insulating ceramic base on the same side as the major surface of the solid electrolyte body on which the reference electrode is disposed. Specifically, the insulating ceramic base is located between the solid electrolyte body and the heating element, thereby ensuring a desired degree of electric insulation between the heating element and the reference electrode.

5 Claims, 14 Drawing Sheets

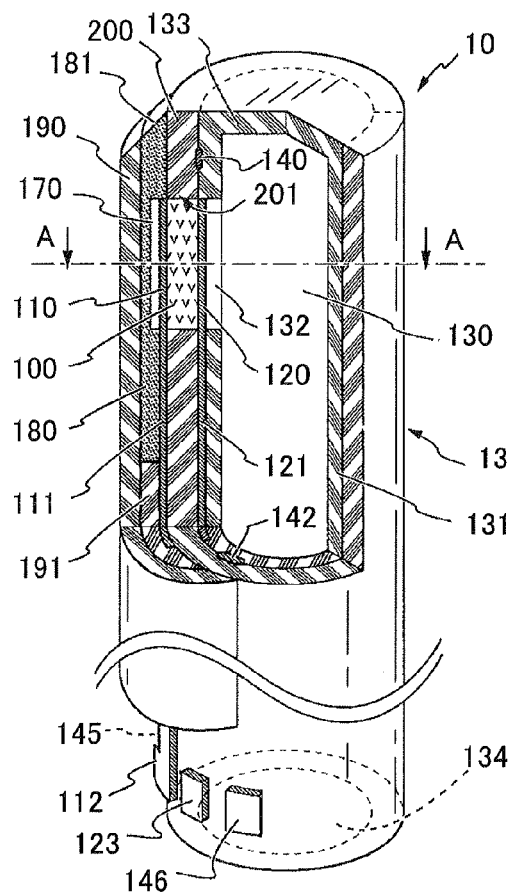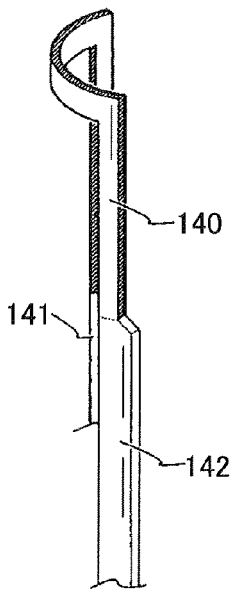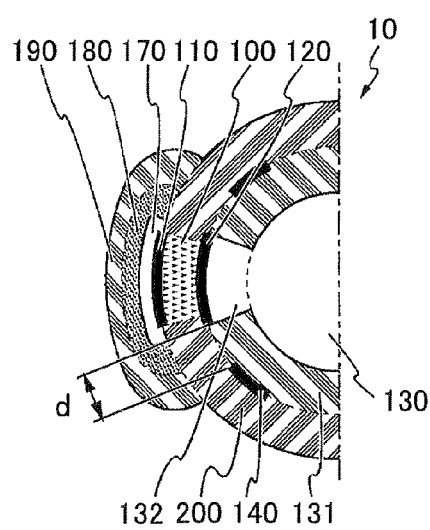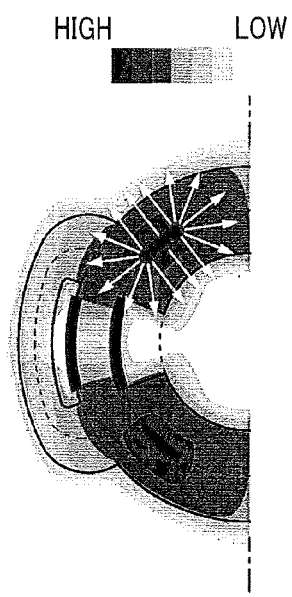

FIG.3(a-1)
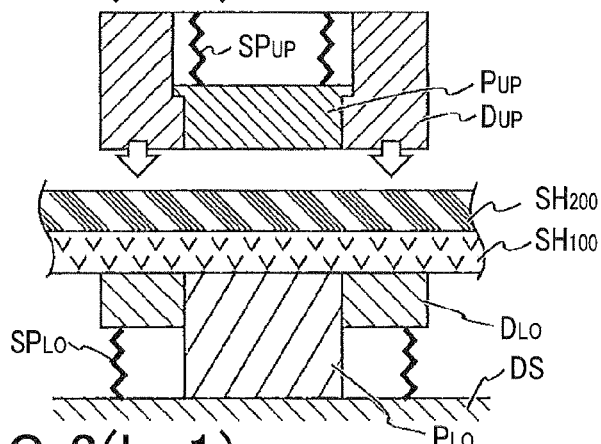
FIG.3(a-2)
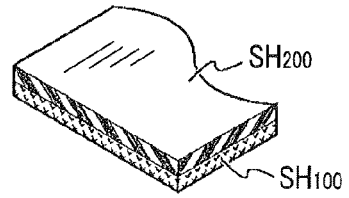
FIG.3(b-1)
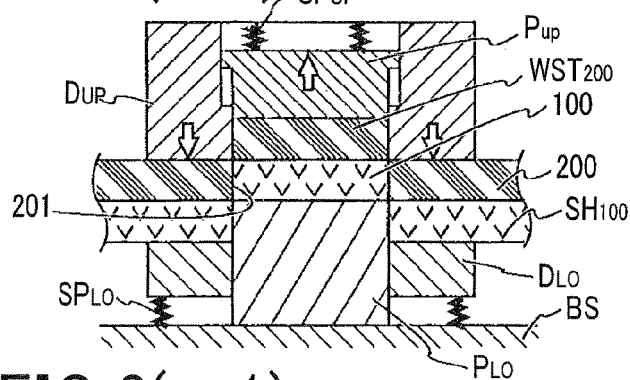
FIG.3(b-2)
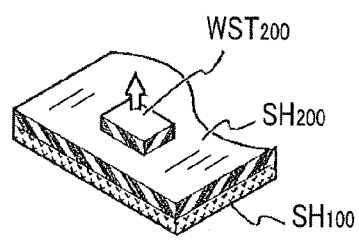
FIG.3(c-1)
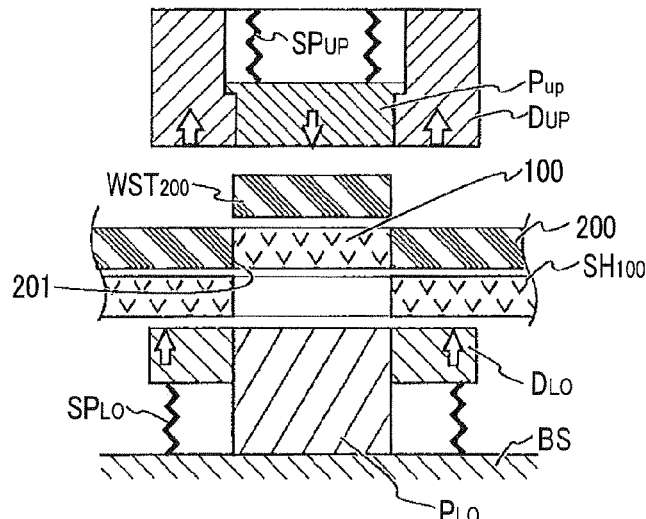
FIG.3(c-2)
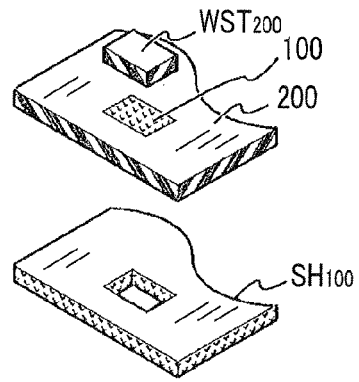
FIG.3(d-1)
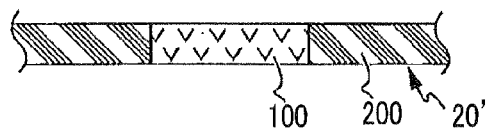
FIG.3(d-2)
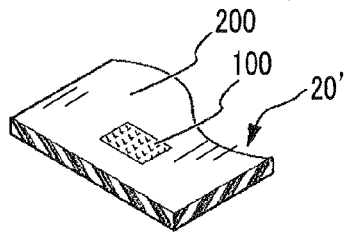

FIG.7(a)
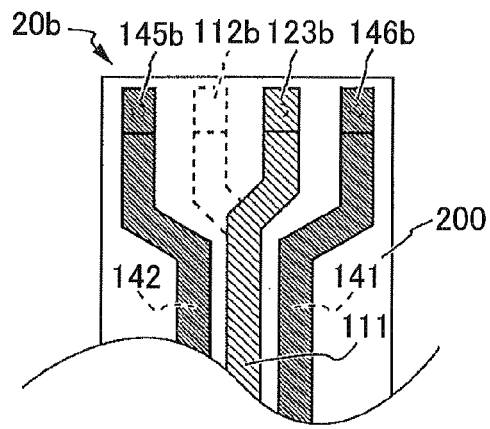
FIG.7(b)
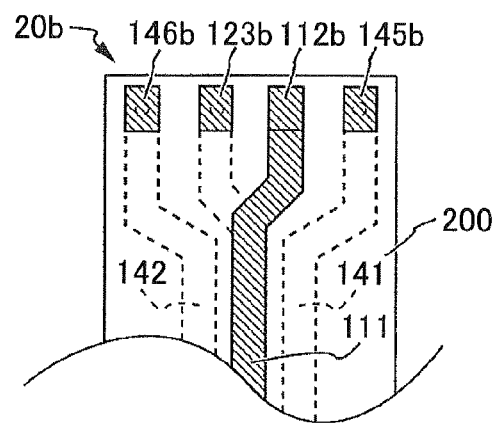
FIG.7(c)
FIG.7(d)
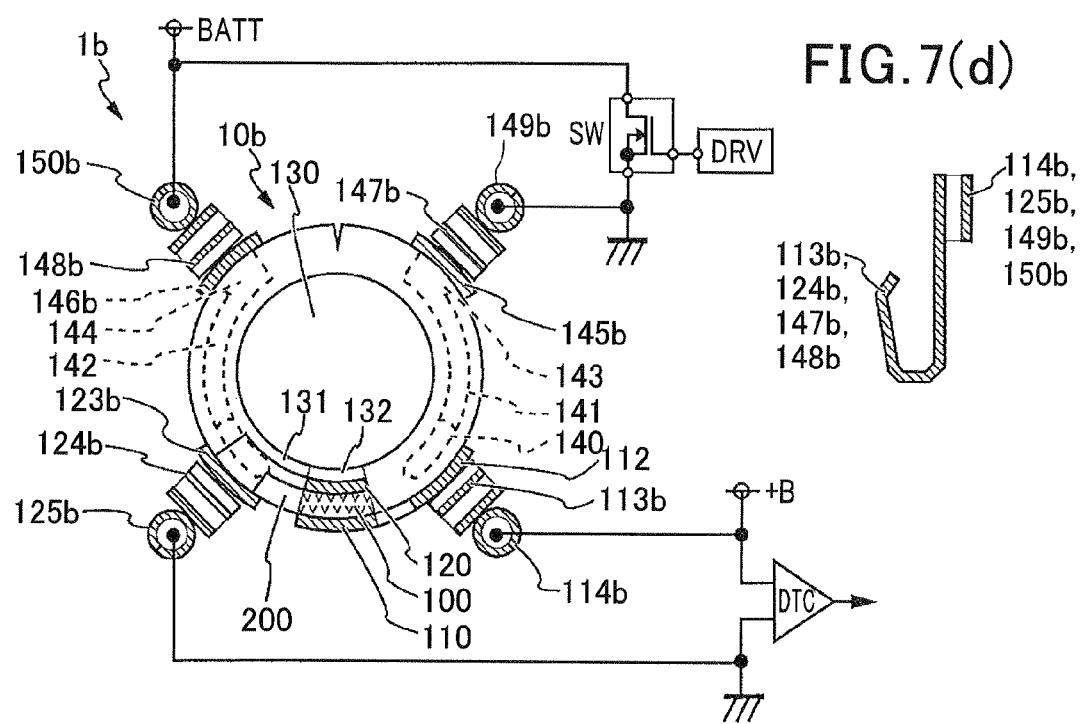

COMPARATIVE EXAMPLE No.1

FIG.9(a)
COMPARATIVE EXAMPLE No.2
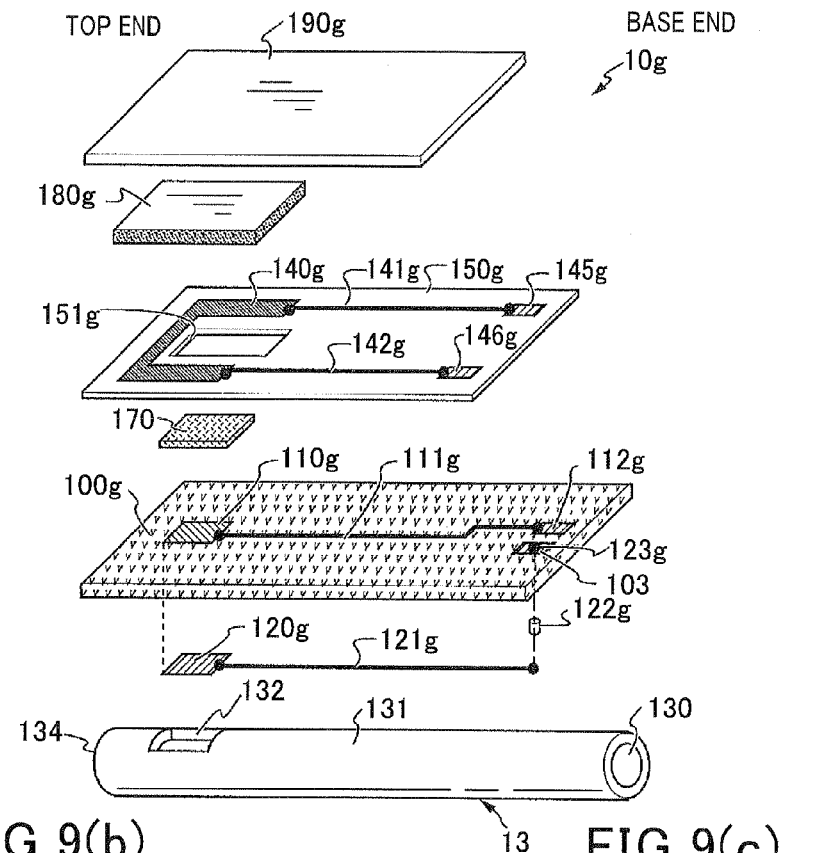
FIG.9(b)
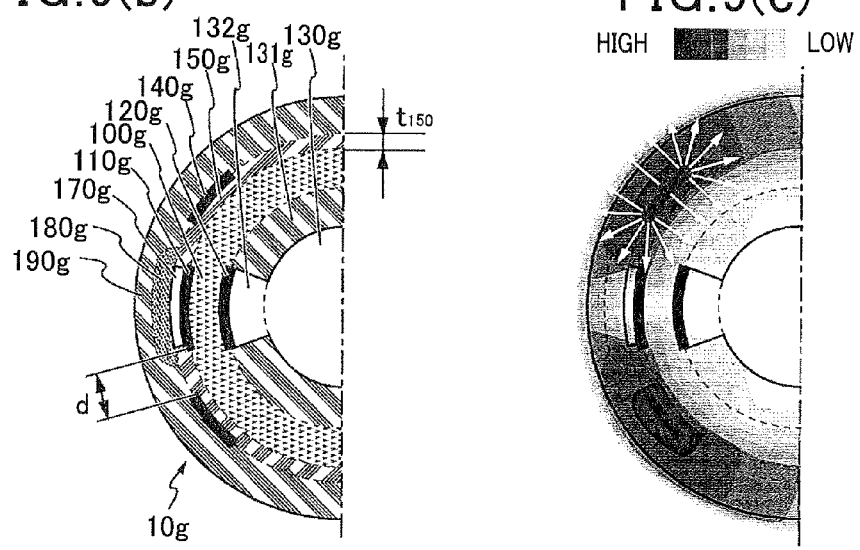
FIG.9(c)

COMPARATIVE EXAMPLE No.3

COMPARATIVE EXAMPLE No.4

COMPARATIVE EXAMPLE No.5

COMPARATIVE EXAMPLE No.6

COMPARATIVE EXAMPLE No.7

GAS SENSOR ELEMENT, GAS SENSOR, AND PRODUCTION METHOD THEREOF

CROSS REFERENCE TO RELATED DOCUMENT

The present application claims the benefit of Japanese Patent Application No. 2011-210167 filed on Sep. 27, 2011, the disclosure of which is incorporated herein by reference.

BACKGROUND

1. Technical Field

The present disclosure relates generally to a gas sensor element which may be installed in an exhaust pipe of an internal combustion engine to measure the concentration of a specified component of exhaust emissions of the engine, and more particularly to a gas sensor equipped with a solid electrolyte body which at least exhibits oxygen ion conductivity and has a pair of electrode layers formed on opposed surfaces thereof and an electrically activated heater. The disclosure also relates to a gas sensor equipped with the above type of gas sensor element and production method thereof.

2. Background Art

A gas sensor element is known which is disposed in an exhaust path extending from an internal combustion engine, such as automotive engine, to measure a specified gas component of exhaust emissions, such as oxygen, nitrogen oxide (NOx), ammonia, or hydrogen, for controlling the burning of fuel in the engine or an operation of an exhaust emission control system.

Japanese Patent First Publication No. H01-253649 discloses the above type of gas sensor element equipped with a solid electrolyte body and a heating element stacked on the solid electrolyte body. The solid electrolyte body has a measurement gas-exposed electrode and a reference gas-exposed electrode. The measurement gas-exposed electrode is formed on a surface of the solid electrolyte body to be exposed to gas to be measured (which will also be referred to as a measurement gas below). The reference gas-exposed electrode is also formed on another surface of the solid electrolyte body to be exposed to a reference gas chamber filled with a reference gas. The gas sensor element is produced by firing a sensor layer and a heater layer to make a laminate of the solid electrolyte body and the heating element. The heating element works to heat the whole of the solid electrolyte body quickly to activate it. This type of gas sensor element is usually called a planar gas sensor element.

Japanese Patent First Publication No. 2002-228626 discloses a solid electrolyte oxygen sensor element which is made of a laminate of a sensing portion, an insulating layer, and a heating portion stacked on the sensing portion through the insulating layer. The heating portion is equipped with a heating element working to activate the sensing portion to measure the concentration of oxygen correctly. The insulating layer avoids the leakage of current from the heating element to the sensing portion.

Japanese Patent Second Publication No. 06-048258 discloses an oxygen concentration sensor equipped with a hollow insulating ceramic cylinder, an oxygen concentration measuring device, a sheet assembly, and an insulating protective layer. The insulating ceramic cylinder has a closed end and an open end. The insulating ceramic cylinder also has defined therein a reference gas chamber leading to the open end. The insulating ceramic cylinder also has an opening formed in a peripheral wall thereof in communication with the reference gas chamber. The oxygen concentration measuring device is fit in the opening of the insulating ceramic cylinder and equipped with electrodes affixed to opposed surfaces thereof. One of the electrode faces outwardly of the insulating ceramic cylinder, while the other electrode faces inwardly of the insulating ceramic cylinder. The sheet assembly is made up of an insulating sheet and heater leads and electrode leads affixed to the insulating sheet. The heater leads and the electrode leads are formed by metallic films. The insulating sheet also has an opening. The sheet assembly is wrapped around the periphery of the insulating ceramic cylinder with the opening facing the oxygen concentration measuring device. The protective layer is porous and disposed over the closed end and the opening of the insulating ceramic cylinder. The insulating ceramic cylinder and the sheet assembly are fired together. One of the opposed surfaces of the oxygen concentration measuring device is exposed to the reference gas chamber, while the other surface is exposed to the gas to be measured through the protective layer.

FIGS. 8(a), 8(b), and 8(c) illustrates a gas sensor element 10g, like in Japanese Patent First Publication No. H01-253649. The gas sensor element 10g will also be described later as a comparative example No. 1.

The gas sensor element 10z is of a planar type and includes a heating element 140z, and a solid electrolyte layer 100, and a reference gas chamber 130z formed between the heating element 140z and the solid electrolyte layer 100. Air, which is highly electrically insulating, is admitted into the reference gas chamber 130z. The air in the reference gas chamber 130z obstructs transmission of heat, as produced by the heating element 140z, to the solid electrolyte layer 100z, thus resulting in a lag in activating the solid electrolyte layer 100z to measure the gas correctly.

The gas sensor element 10z is in the form of a planar plate which is typically susceptible to breakage due to thermal stress. It is, thus, necessary to increase the thickness of insulating layers 150z and 160z in order to improve the durability of the gas sensor element 10z. This, however, results in an increase in overall size of the gas sensor element 10z, which leads to a drop in thermal efficiency and an increased lag in activating the gas sensor element 10z.

The oxygen gas sensor, as taught in the above described Japanese Patent First Publication No. 2002-228626, has the insulating layer between the sensing portion and the heating portion. The insulating layer is formed by firing a green sheet or using screen printing techniques.

Thinning the insulating layer in a production process thereof may cause defects such as pinholes to be developed. The measurement gas, thus, passes through the pinholes and reaches the heating element. The heating element may react with contaminants in the measurement gas and then sublimate, thus resulting in a deterioration thereof. Increasing the thickness of the insulating layer in order to increase the resistance of the heating element to the oxidation for ensuring a required lifespan thereof will result in an increase in overall size of the oxygen gas sensor. Lots of thermal energy is, thus, needed to heat the insulating layer. In other words, lots of time is consumed to heat and activate the solid electrolyte layer.

The oxygen concentration sensor, as taught in the above described Japanese Patent Second Publication No. 06-048258, is equipped with the insulating ceramic cylinder with the opening formed in the peripheral wall thereof. The opening has an inner shoulder serving as a seat on which the oxygen concentration measuring device made of a solid electrolyte body is fit. The oxygen concentration measuring device has the electrodes affixed to the opposed surfaces thereof. Such an arrangement of the oxygen concentration measuring device results in complexity of layout of the electrode leads, which may lead to cracks in the electrode leads, the insulating ceramic cylinder, and the solid electrolyte body when being fired.

Japanese Patent Second Publication No. 06-048258 also teaches the insulating sheet made up of two discrete sheets: one being a heater carrier sheet on which the heating element is formed, and the other being an electrode carrier sheet on which the heater leads and the electrode leads are formed. The heater carrier sheet and the electrode carrier sheet are affixed separately to the insulating ceramic cylinder, thus resulting in a lack in transmitting the thermal energy produced by the heating element to the electrode carrier sheet. This leads to a lag in activating the oxygen concentration sensor. Additionally, it is also necessary to affix the heater carrier sheet and the electrode carrier sheet to the insulating ceramic cylinder so as not to overlap each other. This contributes to inconvenience in production of the oxygen concentration sensor.

SUMMARY

It is therefore an object of the disclosure to provide a gas sensor element which works to measure a specified component of gas and designed to have a quickly activatable/easy-to-manufacture structure and/or exhibit an increased degree of durability.

It is another object of the disclosure to provide a gas sensor equipped with the above type of gas sensor element and a production method of the gas sensor element.

According to one aspect of the invention, there is provided a gas sensor element which may be employed in automotive vehicles to measure the proportion of oxygen ($O_2$) in exhaust gas emitted from an internal combustion engine for control of an air-fuel ratio in the engine.

The gas sensor element comprises: (a) an insulating ceramic member which has surfaces opposed to each other and a through hole formed therein; (b) a solid electrolyte body which is disposed in the hole of the insulating ceramic member and works to conduct to at least a given ion, the solid electrolyte body having a first major surface and a second major surface; (c) a measuring electrode disposed on the first major surface of the solid electrolyte body to be exposed to the gas; (d) a reference electrode disposed on the second major surface of the solid electrolyte body to be exposed to a reference gas; and (e) a heating element disposed on one of the opposed surfaces of the insulating ceramic member on the same side as the second major surface of the solid electrolyte body. The heating element works to activate the solid electrolyte body.

Specifically, the insulating ceramic member, which is highly electrically insulating is disposed between the solid electrolyte body and the heating element, thereby ensuring a desired degree of electric insulation between the heating element and the reference electrode. This minimizes the leakage of current from the heating element to the reference electrode to ensure the stability in operation of the gas sensor element.

When the heating element is actuated, the thermal energy produced by the heating element is transmitted to the solid electrolyte body through the insulating ceramic member, which has a high thermal conductivity, thus accelerating the activation of the solid electrolyte body and establishing the stability in operation of the gas sensor element quickly.

The heating element is disposed on the surface of the insulating ceramic member on the same side as the second major surface of the solid electrolyte body. The insulating ceramic member, thus, serves as a mechanical support for the heating element and a protective or shield member for isolating the heating element from the gas. This structure improves the service life of the heating element and permits the overall size of the gas sensor element to be reduced.

In the preferred mode of the embodiment, the gas sensor element may further include a hollow cylindrical ceramic member which has a closed end and defines therein a reference gas chamber into which the reference gas is admitted. The hollow cylindrical ceramic member also has formed in a peripheral surface thereof a window which communicates with the reference gas chamber. The insulating ceramic member is stacked on the hollow cylindrical member with the solid electrolyte body exposed to the reference gas chamber through the window. The heating member is interposed between the hollow cylindrical ceramic member and the insulating ceramic member.

In other words the heating element is covered with the insulating ceramic member and the cylindrical ceramic member and thus protected from the gas and the reference gas, thereby enhancing the stability in operation of the gas sensor element. Additionally, use of the cylindrical ceramic member also improves the mechanical strength of the gas sensor element and resistance to thermal stress breakage arising from being splashed with, for example, water.

The heating element may be located at a given insulating interval away from one of the solid electrolyte body and the reference electrode. In other words, the heating element is away from the reference electrode as well as the solid electrolyte body, thus enables the solid electrolyte body to be activated quickly without sacrificing the electric insulation from the heating element. The insulating interval may be defined as a distance which is the shorter of a minimum distance between a peripheral edge of the heating element and a peripheral edge of the solid electrolyte body and a minimum distance between the peripheral edge of the heating element and a peripheral edge of the reference electrode and greater than or equal to 0.1 mm and smaller than or equal to 3 mm.

In the case where the insulating interval is less than 0.1 mm, the current may leak from the heating element to the solid electrolyte body and/or the reference electrode, which results in instability in operation of the gas sensor element. Alternatively, in the case where the insulating interval is greater than 3.0 mm, the overall size of the gas sensor element is increased. It, therefore, takes much time to activate the solid electrolyte body through the heating element.

The solid electrolyte body may be made of a partially-stabilized zirconia, thereby enhancing quick activation of the solid electrolyte body and improving the durability of the gas sensor element.

The insulating ceramic member may be made of alumina. The use of alumina enhances the electric insulation and thermal conductivity, thereby enhancing the quick activation of the solid electrolyte body further.

According to the second aspect of the embodiment, there is provided a gas sensor which works to measure a given component of gas which comprises: (1) a gas sensor element including (a) an insulating ceramic member which has surfaces opposed to each other and a through hole formed therein, (b) a solid electrolyte body which is disposed in the hole of the insulating ceramic member and works to conduct to at least a given ion, the solid electrolyte body having a first major surface and a second major surface, (c) a measuring electrode disposed on the first major surface of the solid electrolyte body to be exposed to the gas, (d) a reference electrode disposed on the second major surface of the solid electrolyte body to be exposed to a reference gas, and (e) a heating element disposed on one of the opposed surfaces of the insulating ceramic member on the same side as the second major surface of the solid electrolyte body, the heating element working to activate the solid electrolyte body; (2) a first and a second signal line leading to the reference electrode and the measuring electrode for transmitting a sensor output to an external detection circuit; (3) a first and a second conductor leading to the heating element for establishing electric connections with an external power supply control circuit to control supply of electric power to the heating element; and (4) a housing in which the gas sensor element, the first and second signal line, and the power supply conductors are retained. The housing is designed to hold the gas sensor element to be exposed to the gas.

The above structure of the gas sensor is capable of activating the gas sensor element quickly and ensures the stability in operation and mechanical durability of the gas sensor element. The structure is also easy to assemble and permits the size thereof to be reduced.

According to third aspect of the embodiment, there is provided a gas sensor element production method which comprises: (a) forming an insulating ceramic member which is planar and made of an electrically insulating ceramic material, the insulating ceramic member having opposed surfaces and a through hole; (b) forming a solid electrolyte body in the through hole of the insulating ceramic member, the solid electrolyte body being made of a ceramic material which conducts at least a given ion and having a first major surface and a second major surface; (c) forming a measuring electrode disposed on the first major surface of the solid electrolyte body to be exposed to the gas; (d) forming a reference electrode disposed on the second major surface of the solid electrolyte body to be exposed to a reference gas; (e) arranging a heating element disposed on one of the opposed surfaces of the insulating ceramic member on the same side as the second major surface of the solid electrolyte body, the heating element working to activate the solid electrolyte body; (f) preparing a hollow cylindrical ceramic member which is made of an electrically insulating ceramic material and has a closed end and an open end, the hollow cylindrical ceramic member also having a window formed in a peripheral surface thereof; (g) wrapping the insulating ceramic member around the hollow cylindrical ceramic member with the reference electrode facing the window of the hollow cylindrical ceramic member; and (h) firing the hollow cylindrical ceramic member around which the insulating ceramic member is wrapped.

The above production method achieves quick activation of the gas sensor element and improves the durability thereof.

The forming steps of the insulating ceramic member and the solid electrolyte body may prepare a stack of a planar solid electrolyte material and a planer insulating ceramic material and punch the stack to make the through hole in the insulating ceramic member and the solid electrolyte body cut from the planar solid electrolyte material to have a size substantially identical with that of the through hole and simultaneously to place the solid electrolyte body in the through hole, thereby simplifying the production process of the gas sensor element.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 1($a$) is a partially longitudinal sectional view which shows a gas sensor element according to an embodiment;

FIG. 1($b$) is a perspective view which shows a heating element installed in the gas sensor element of FIG. 1($a$);

FIG. 1($c$) is a partially transverse sectional view, taken along the line A-A in FIG. 1($a$);

FIG. 1($d$) is a view which represent a temperature distribution in the gas sensor element of FIG. 1($c$);

FIGS. 3($a$-1), 3($b$-1), 3($c$-1), and 3($d$-1) are partially longitudinal sectional views which illustrate a sequence of punching step of producing an assembly of a solid electrolyte body and an insulating ceramic base which is installed in the gas sensor element of FIGS. 1($a$) to 1($d$);

FIGS. 3($a$-2), 3($b$-2), 3($c$-2), and 3($d$-2) are partially perspective views which illustrate products in the punching steps, as illustrated in FIGS. 3($a$-1), 3($b$-1), 3($c$-1), and 3($d$-1), respectively;

FIG. 5($b$) is a longitudinal sectional view which of FIG. 5($a$);

FIG. 5($c$) is a plane view which illustrates a surface of an insulating ceramic base of the gas sensor element of FIGS. 1($a$) to 1($d$) on which a reference electrode and a heating element are disposed;

FIG. 5($d$) is a sectional view which shows how to wrap the insulating ceramic base of FIGS. 5($a$) to 5($c$) around a cylindrical ceramic base;

FIG. 6($b$) is a partially longitudinal sectional view which of FIG. 6($a$);

FIG. 6($c$) is a partially plane view which illustrates a surface of an insulating ceramic base of the gas sensor element of FIGS. 6($a$) and 6($b$) on which a measuring electrode is disposed;

FIG. 6($d$) is a partially transverse sectional view of the gas sensor element of FIGS. 6($a$) to 6($c$);

FIG. 6($e$) is a partially transverse sectional view which shows the insulating ceramic base of FIGS. 6($a$) to 6($e$) wrapped around a cylindrical ceramic base;

FIGS. 7($a$) and 7($b$) are partially side views which illustrate leads affixed to an insulating ceramic base of a modified form of a gas sensor element;

FIG. 7($c$) is a transverse sectional view which illustrates the insulating ceramic base wrapped around a cylindrical ceramic base and electric connections with an external power supply control circuit and an external detector circuit;

FIG. 7($d$) is a longitudinal sectional view which shows a spring connector for use in establishing electric connections of the gas sensor element with the external power supply control circuit and the external detector circuit of FIG. 7($c$);

FIG. 8($b$) is a partially transverse sectional view, as taken along the line A-A in FIG. 8($a$);

FIG. 8($c$) is a partially transverse sectional view which represent a temperature distribution in the gas sensor element of FIGS. 8($a$) and 8($b$);

FIG. 9($a$) is an exploded perspective view which shows a comparative example No. 2 of a gas sensor element;

FIG. 9(b) is a partially transverse sectional view of the gas sensor element of FIG. 9(a);

FIG. 9(c) is a partially transverse sectional view which represent a temperature distribution in the gas sensor element of FIGS. 9(a) and 9(b);

DESCRIPTION OF THE PREFERRED EMBODIMENTS

Figure 2:
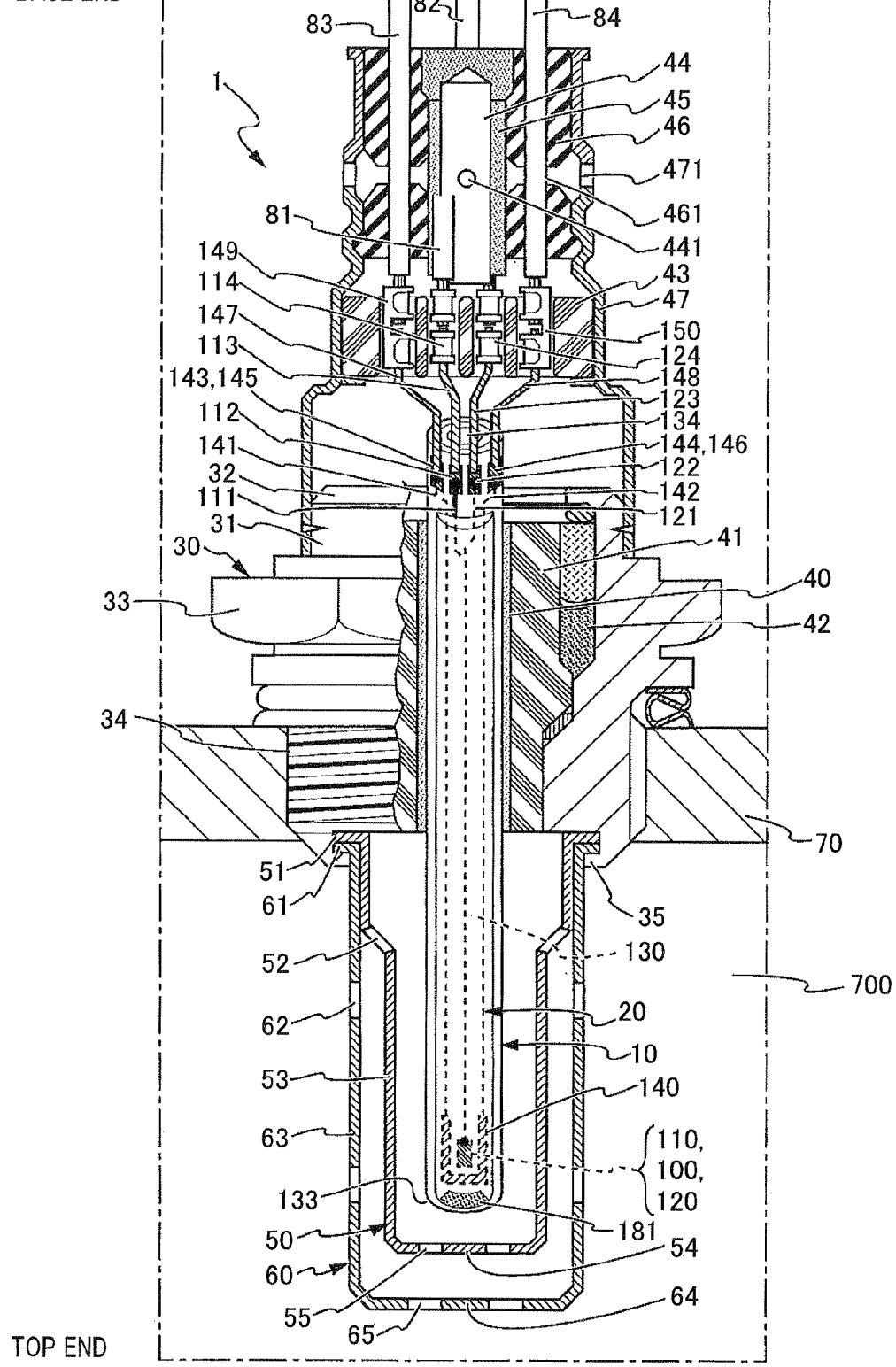
FIG. 2 is a longitudinal sectional view which illustrates a gas sensor equipped with the gas sensor element of FIGS. 1($a$) to 1($d$)

Referring now to the drawings, wherein like reference numbers refer to like parts in several views, particularly to FIGS. 1(a) to 1(d), there is shown a gas sensor element 10 according to the first embodiment.

The gas sensor element 10 may be mounted in a so-called A sensor which measures the proportion of oxygen ($O_2$) in exhaust gas (which will also be referred to as measurement gas below) emitted from an internal combustion engine or a gas sensor for use in measuring the concentration of nitrogen oxide (NOx), sulfur oxide (SOx), carbon hydride (HC), or carbon monoxide (CO) contained in the exhaust gas for control of an air-fuel ratio in the engine.

The following discussion will refer to the gas sensor element 10 as being made of a solid electrolyte material having an oxygen ion conductivity installed in, for example, an oxygen sensor.

The gas sensor element 10, as illustrated in FIGS. 1(a) and 1(b), is made up of a sensor/heater laminate sheet 20 and a bottomed hollow cylindrical ceramic base 13. The sensor/heater laminate sheet 20 is wrapped about the cylindrical ceramic base 13 and made up of a solid electrolyte body 100, a measuring electrode 110, a measuring electrode lead 111, a measuring electrode terminal 112, a reference electrode 120, a reference electrode lead 121, a reference electrode terminal 122, a heating element 140, heater leads 141 and 142, power supply terminals 145 and 146, a measurement gas chamber 170, a diffusion resistance layer 180, a slant measurement gas inlet surface 181, a shield layer 190, a buffer layer 191, and an insulating ceramic base 200. The cylindrical ceramic base 13 is made up of a reference gas chamber 130, a peripheral side wall 131, a through hole 132, and a closed end 133.

The solid electrolyte body 100 has opposed major surfaces. The measuring electrode 110 which is to be exposed to the measurement gas is disposed on one of the major surfaces of the solid electrolyte body 100. The reference electrode 120 which is to be exposed to air admitted into the gas sensor element 10 as a reference gas is mounted on the other major surface of the solid electrolyte body 100. The solid electrolyte body 100, the measuring electrode 110, and the reference electrode 120 constitute a sensing mechanism which will also be referred to as a sensing portion below.

The insulating ceramic base 200 is made from a ceramic material such as alumina having electric insulation properties. The insulating ceramic base 200 is identical in thickness with the solid electrolyte body 100. The solid electrolyte body 100 is in the form of a layer and fit in a through hole (i.e., a window) 201 formed in the insulating ceramic base 200. The major surface of solid electrolyte body 100 may be laid flush with, slightly protrude, or slightly sinks from the surface of the insulating ceramic base 200.

The cylindrical ceramic base 13 is made of a ceramic material such as alumina having electric insulation properties and has the closed end 133 and an open end 134 opposed to the closed end 133. The cylindrical ceramic base 13 has defined thererein the reference gas chamber 130 into which the air is admitted as the reference gas. The cylindrical ceramic base 13 also has the through hole 312 formed in a portion of the side wall 131 which is closer to the closed end 133 than to the open end 134.

The insulating ceramic base 200 is wrapped about the outer periphery of the cylindrical ceramic base 13. The holes 201 and 132 are in coincidence with each other. The reference electrode 120 disposed on the surface of the solid electrolyte body 100 faces the hole 132 and is exposed directly to the air in the reference gas chamber 130.

The measuring electrode 110 disposed on the solid electrolyte body 100 faces the measurement gas chamber 170. Specifically, the measurement gas chamber 170 surrounds the whole of a major surface of the measuring electrode 110. The measuring electrode 110 is exposed directly to the reference gas in the reference gas chamber 170.

The measuring electrode 110 and the reference electrode 120 are coupled to the measuring electrode lead 111 and the reference electrode lead 121, respectively, which connect with an external power supply (not shown) and a detector circuit or a controller (not shown).

Figure 4:
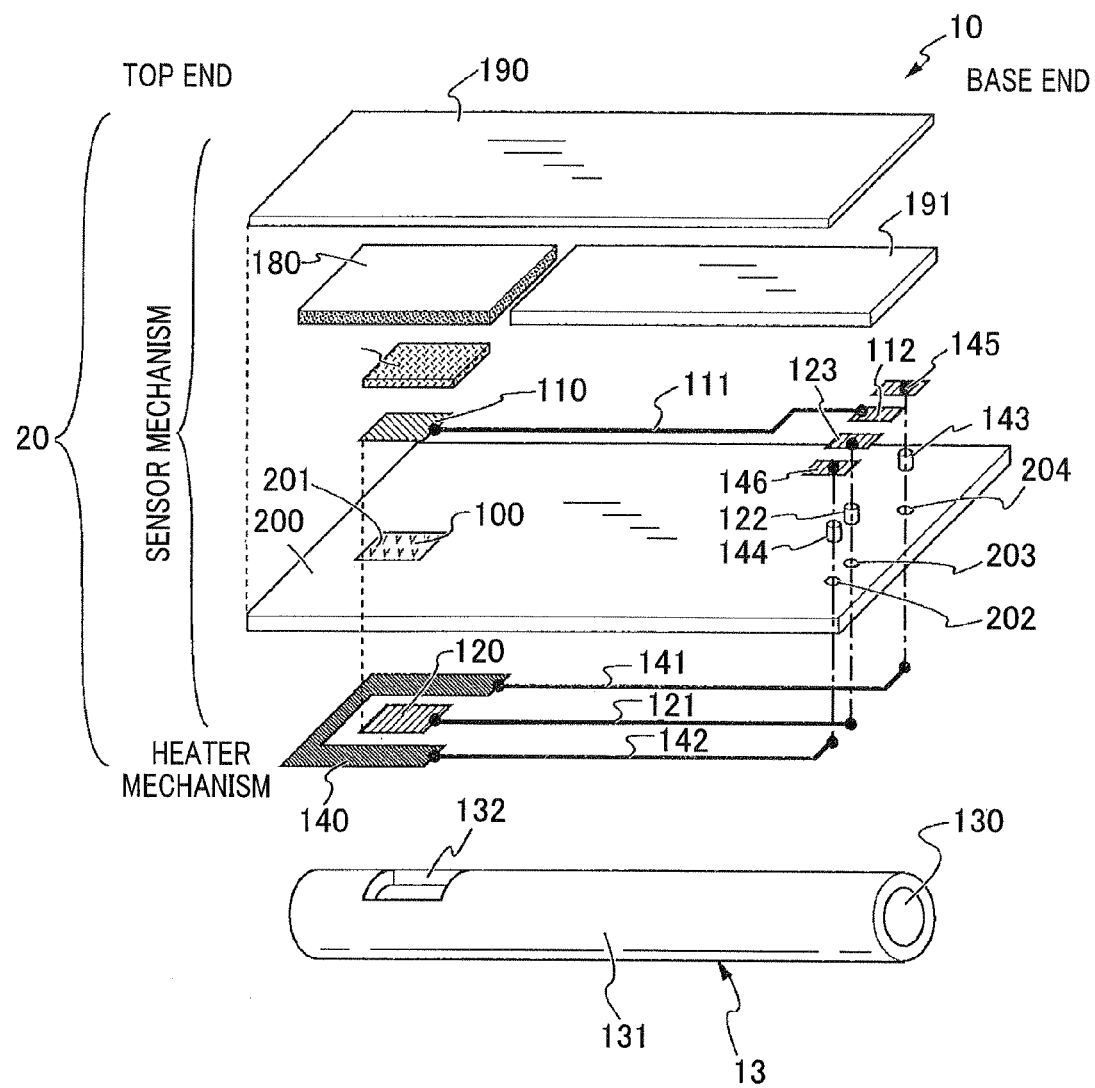
FIG. 4 is an exploded perspective view which illustrates the gas sensor element of FIGS. 1($a$) to 1($d$)

The heating element 140 is, as clearly illustrated in FIG. 4, of a substantially C-shape and affixed to the major surface of the insulating ceramic base 200 which lies flush with the reference electrode 120 on the solid electrolyte body 100. The heating element 140 is, as can be seen in FIG. 1(c), located at an electrically insulating interval d away from the reference electrode 120 and embraces, as illustrated in FIG. 4, the periphery of the measuring electrode 110. The solid electrolyte body 100 may have a width greater than that of the reference electrode 120 in a circumferential direction of the gas sensor element 10. In this case, the insulating interval d is a distance between the heating element 140 and the solid electrolyte body 100. In other words, the insulating interval d is the shorter of a minimum distance between the inner edge of the heating element 140 and the outer edge of the reference electrode 120 and a minimum distance between the inner edge of the heating element 140 and the outer edge of the solid electrolyte body 100.

The heating element 140 is interposed between bonded surfaces of the cylindrical ceramic base 13 and the insulating ceramic base 200.

The heating element 140 is connected at ends thereof to the heater leads 141 and 142 which are joined to the external power supply and an energization controller (which is not shown and will also be referred to as a power supply control circuit below) through heater terminals 143 and 144. When energized, the heating element 140 produces thermal energy to elevate the temperature of the sensing mechanism (i.e., the solid electrolyte body 100, the measuring electrode 110, and the reference electrode 120) up to a value at which the sensing mechanism is placed in a desirable activated state.

The diffusion resistance layer 180 is made of a porous material having a given diffusion resistance and disposed over the whole of the measurement gas chamber 170. The shield layer 190 is affixed to cover the entire outer surface of the diffusion resistance layer 180 except the slant measurement gas inlet surface 181.

The slant measurement gas inlet surface 181 is formed by a tapered end of the diffusion resistance layer 180 which is exposed directly outside the gas sensor element 10 and through which the measurement gas is admitted into the measurement gas chamber 170.

The shield layer 190 and the buffer layer 191 serve to shield the measuring electrode lead 111 from the measurement gas and also to avoid leakage of the measurement gas flowing through the diffusion resistance layer 180 to the outside of the gas sensor element 10.

Tests were performed as will be described later in detail, and the following facts were found.

The solid electrolyte body 100 is, as described above, embedded in the insulating ceramic base 200. The heating element 140 is disposed on the major surface of the insulating ceramic base 200 which lies flush with the reference electrode 120 on the solid electrolyte body 100, has the periphery located at the electrically insulating interval d (preferably greater than or equal to 0.1 mm and less than or equal to 3 mm) away from the periphery of the solid electrolyte body 100, and embraces the periphery of the solid electrolyte body 100. Note that when the reference electrode 120 is greater in size than the solid electrolyte body 100, the insulating interval d is, as described above, a distance between the heating element 140 and the reference electrode 120. When the heating element 140 is energized, the solid electrolyte body 100 is, as illustrated in FIG. 1(c), heated directly by the thermal energy, as transmitted through the insulating ceramic base 200, and activated quickly.

The partially-stabilized zirconia that is material of the solid electrolyte body 100 is low in thermal conductivity (i.e., 2 to 3 W/m·K). A range in which the thermal conductivity is low is minimized around the measuring electrode 110 and the reference electrode 120 by embedding the solid electrolyte body 100 in the insulating ceramic base 200 which is high in thermal conductivity (i.e., 20 to 30 W/m·K), thereby resulting in an increased degree of thermal conductivity of the whole of the gas sensor element 10. This accelerates the rise in temperature of the gas sensor element 10. The alumina that is material of the insulating ceramic base 200 is high in electric insulation serves to keep the leakage of electric current to the sensing mechanism low when the heating 140 is energized even if the insulating interval d is shortened. This enables the heating element 140 to be located close to the solid electrolyte body 100, thus resulting in a decreased time required to activate the solid electrolyte body 100.

The heating element 140 is, as described above, interposed between the insulating ceramic base 200 and the cylindrical ceramic base 13, in other words, shielded from the measurement gas, thus avoiding the deterioration thereof arising from poisons contained in the measurement gas and ensuring the stability in operation of the gas sensor element 10.

If the heating element 140 is affixed to the surface of the insulating ceramic base 200 with which the measuring electrode 110 is flush, it results in need for a protective layer to isolate the heating element 140 from the measurement gas, which leads to an increase in overall size of the gas sensor element 10. The above structure of the gas sensor element 10 eliminate the need for such a protective layer, thus permitting the size of the gas sensor element 10 to be reduced.

The ceramic base 13 is of a cylindrical shape and thus greater in mechanical strength than the conventional structure in which the gas sensor element 10 is of a planar shape, thus exhibiting the durability great enough to withstand thermal impact arising from being splashed with water.

The gas sensor element 10 has been described as being installed in the gas sensor designed to measure the concentration of oxygen ($O_2$), but however, may be engineered to measure another kind of gas. The gas sensor element 10 may alternatively be made by using $ABO_3$-type transition metal oxide such as $SrZrO_3$ or $SrC3O_3$ having proton conductivity as material of the solid electrolyte body 100, tungsten carbide, silicon nitride, or ruthenium oxide as material of the heating element 140, or titania or spinel as material of the insulating ceramic base 200.

The surface of the gas sensor element 10 may be covered with a porous protective layer which is formed by heat-resisting ceramic particles using dipping or plasma spraying techniques for minimizing the risk of breakage due to being splashing with water or deterioration due to being subjected to poisons.

FIG. 2 illustrates a gas sensor 1 in which the gas sensor element 10 is mounted.

The gas sensor element 10, as described above, has the sensor/heater laminate sheet 20 wrapped about the cylindrical ceramic base 13. The cylindrical ceramic base 13 is oriented in the gas sensor 1 with the closed end 133 facing the top end (i.e., the head) of the gas sensor 1 and the open end 134 facing the base end (i.e., an upper end, as viewed in FIG. 2) of the gas sensor 1. The cylindrical ceramic base 13 is disposed inside a hollow cylindrical insulator 41 made from an electrically insulating ceramic material such as alumina and retained firmly therein by a heat-resisting bond 40 such as ceramic cement or heat-resisting glass. The assembly of the ceramic base 13 and the insulator 41 (i.e., the gas sensor element 10) is disposed in a hollow cylindrical housing 30. The gas sensor element 10 has a top end portion which protrudes outside the housing 30 and is exposed to the measurement gas. The top end portion works as a sensing portion which is sensitive to the measurement gas.

The insulator 41 is retained firmly inside the housing 30 through a sealant 42 such as talc. The housing 30 is made of a hollow cylindrical metallic member such as stainless steel.

The housing 30 has a top end and a base end. A cup-shaped double-walled protective cover assembly is secured to the top end of the housing 30. The cover assembly is made up of a bottomed inner cover 50 and a bottomed outer cover 60 enclosing the inner cover 50 coaxially. The inner cover 50 and the outer cover 60 have base ends shaped into flanges 51 and 61. The flanges 51 and 61 are grasped firmly by elastically bending or crimping a cylindrical extension 35 (which will also be referred to as a crimped portion below) formed on the top end of the housing 30 to make a firm joint of the cover assembly to the housing 30.

The gas sensor 1 also include a hollow cylindrical casing 47 made of a metallic material such as stainless steel. The casing 47 is fit on a boss 31 formed on the base end of the housing 30 and holds therein signal lines 81 and 82 and power supply lines (which will also be referred to as power supply conductors below) 83 and 84 to be insulated from each other through an insulator 43. The signal lines 81 and 82 and the power supply lines 83 and 84 are also retained air-hermetically in the casing 47 through a sealing rubber 46, a water-repellent filter 45, and a support 44. The water-repellent filter 45 is fit on the support 44. The signal lines 81 and 82 and the power supply lines 83 and 84 are electrically joined through connecting terminals 113, 123, 147, and 148 and metallic connectors (e.g., crimping terminals) 114, 124, 149, and 150 to the measuring electrode terminal 112, the reference electrode terminal 122, and the power supply terminals 145 and 146, respectively, which extend from the base end of the gas sensor element 10. The signal lines 81 and 82 are used to transmit a sensor output to the detector circuit, as described above. The power supply lines 83 and 84 are used to supply electric power from the external power supply to the heating element 140.

The casing 47 has reference gas inlet holes 471 formed in a side wall thereof. The sealing rubber 46 has reference gas inlet holes 461 formed through a side wall thereof. The support 44 also has reference gas inlet holes 441 formed through a side wall thereof. The reference gas inlet holes 471, 461, and 441 communicate with each other to define a reference gas inlet path through which the air (i.e., the reference gas) is admitted into the reference gas chamber 130. The water-repellent filter 45 serves to prevent water or moisture from entering the reference gas chamber 130.

The inner and outer covers 50 and 60 are, as described above, of a cup-shape and have bottom surfaces 54 and 64 (i.e., top end surfaces in FIG. 2), respectively. The inner and outer covers 50 and 60 are laid coaxially with each other to form the double-walled protective cover assembly. The inner cover 50 has gas inlet holes 52 and 55 formed in a side surface 53 and the bottom surface 54. Similarly, the outer cover 60 has gas inlet holes 62 and 65 formed in a side surface 63 and the bottom surface 64. The gas inlet holes 52, 55, 62, and 65 work to control the velocity of the measurement gas flowing into or outside the cover assembly of the inner and outer covers 50 and 60. The top end portion (i.e., the sensing portion) of the gas sensor element 10 is exposed to the measurement gas within the cover assembly to produce an output as a function of the concentration of, for example, $O_2$ of the measurement gas.

The housing 30 has an external thread 34 formed on a top end portion thereof. The thread 34 is fastened into a wall of a gas flow pipe 70 (i.e., an exhaust pipe extending from an internal combustion engine) to have the sensing portion of the gas sensor element 10 exposed to the measurement gas 700.

The insulator 41, the housing 30, the casing 47, and the inner and outer covers 50 and 60 are not limited to the above structures, but may be designed to have another known structures, respectively.

In an operation of the gas sensor 1, when supplied with the electric power through the external power supply control circuit, the heating element 140 produces heat which is, in turn, transmitted to the solid electrolyte body 100 through the insulating ceramic base 200, so that the solid electrolyte body 100 is activated. Upon activation of the solid electrolyte body 100, a potential difference will be developed between the measuring electrode 110 and the reference electrode 120 as a function of a difference in concentration of oxygen ($O_2$) between the measurement gas which has been introduced into the measurement gas chamber 170 through the diffusion resistance layer 180 and the reference gas (i.e., the air) which has been introduced into the reference gas chamber 130. The potential difference is outputted to the detector circuit (not shown) through the signal lines 81 and 82 as representing the concentration of oxygen in the measurement gas. Alternatively, the detector circuit may apply the voltage across the measuring electrode 110 and the reference electrode 120 and monitor a resulting current flowing through the solid electrolyte body 100 as a function of the concentration of oxygen in the measurement gas.

A production method of the gas sensor element 10 will be described below with reference to FIGS. 3(a-1) to 5(d).

The insulating ceramic base 200 made of an insulating ceramic sheet is prepared. A window is drilled in the insulating ceramic base 200 to make the hole 201. The solid electrolyte body 100 is embedded or fit in the hole 201. The measuring electrode 110 and the reference electrode 140 are affixed to the opposed major surfaces of the solid electrolyte body 100. The sensor/heater laminate sheet 20 equipped with the insulating ceramic base 200 and the heating element 140 affixed to the surface of the insulating ceramic base 200 with which the reference electrode 120 lies flush is glued to the periphery of the cylindrical ceramic base 13 in which the reference gas chamber 130 is formed. The sensor/heater laminate sheet 20 is, as apparent from the above discussion, equipped with a sensor function and a heater function and includes at least the solid electrolyte body 100, the measuring electrode 110, the reference electrode 120, the heating element 140, and the insulating ceramic base 200. Specifically, the sensor/heater laminate sheet 20 formed by at least two sheets (i.e., the insulating ceramic base 200 and the shield layer 190) is adhered to the cylindrical ceramic base 13 and then fired to make the gas sensor element 10. The sensor/heater laminate sheet 20 may alternatively be formed by a single sheet. This is accomplished by wrapping a sheet of the insulating ceramic base 200 in which the solid electrolyte body 100 is fit around the cylindrical ceramic base 13 and then forming on the insulating ceramic base 200 the heating element 140, the measuring electrode 110, the reference electrode 120, the measuring gas chamber 170, etc., using coating, plating, or thermal spraying techniques without use of the shield layer 190.

The electrode pattern (i.e., the measuring electrode 110, the reference electrode 120, the heating element 140, etc.) is formed on the planar ceramic sheet (i.e., the insulating ceramic base 200), thus minimizing the probability of electric disconnections or bonding defects thereof. This improves the reliability in operation of the gas sensor element 10.

The production method of the gas sensor element 10 will also be described below in more in detail.

The solid electrolyte body 100 is made from a solid electrolyte material containing, for example, a main component of zirconia (i.e., zirconium dioxide $ZrO_2$) and an additive of yttria (i.e., $Y_2O_3$, 4-8 mol %).

The solid electrolyte material may also contain alumina, silica, magnesia, and/or calcia. These auxiliary agents serve to improve sintering performance of zirconia, bring the degree of shrinkage (also called contraction percentage) or coefficient of thermal expansion of the solid electrolyte material into agreement with those of the material of the insulating ceramic base 200, or enhance the strength of adhesion among the solid electrolyte body 100, the insulating ceramic base 200, the cylindrical ceramic base 13, the measuring electrode 110, and the reference electrode 120.

The insulating ceramic base 200 is made from an insulating ceramic material which preferably contains, for example, a main component of 90 wt % or more of alumina (i.e., aluminum oxide $Al_2O_3$) that is high in thermal conductivity and electric insulation. The alumina may contain zirconia, yttria, magnesia, calcia, and/or silica. These auxiliary agents serve to improve sintering performance of alumina, bring the degree of shrinkage or coefficient of thermal expansion of the alumina into agreement with those of material of the solid electrolyte body 100, or enhance the strength of adhesion among the insulating ceramic base 200, the cylindrical ceramic base 13, the solid electrolyte body 100, the measuring electrode 110, the measuring electrode lead 111, the measuring electrode terminal 112, the reference electrode 120, the reference electrode lead 121, and the reference electrode terminal 122.

First, an unfired ceramic sheet $SH_{200}$ (i.e., an unfired alumina sheet) which will be the insulating ceramic base 200 is produced. The unfired ceramic sheet $SH_{200}$ will also be referred to as a planer insulating ceramic material or an alumina sheet below.

The alumina sheet $SH_{200}$ is formed by blending or combining alumina powder with sintering additive such as magnesia powder, binder such as butyral resin, and plasticizer such as BBP (butyl benzyl phthalate) to make alumina slurry, shaping the alumina slurry using a doctor blade into a sheet, and then volatilizing organic solvent therefrom.

The hole 201 in which the solid electrolyte body 100 is to be fit is formed in the alumina sheet $SH_{200}$. Through holes 202, 203, and 204 are also drilled in the alumina sheet $SH_{200}$ to make the via-conductors 144, 122, and 143. The via-conductor 122 is the reference electrode terminal, as described above, and will also be referred to as a reference electrode via-conductor below.

An unfired solid electrolyte sheet $SH_{100}$ (i.e., an unfired zirconia sheet) which will be the solid electrolyte body 100 is produced. The unfired solid electrolyte sheet $SH_{100}$ will also be referred to as a planar solid electrolyte material or a zirconia sheet below.

The zirconia sheet $SH_{100}$ is formed by blending or combining zirconia powder with yttria powder, binder such as butyral resin, and plasticizer such as BBP (butyl benzyl phthalate) and mixing organic solvent with it to made zirconia slurry, shaping the zirconia slurry using a doctor blade into a sheet, and then volatilizing organic solvent therefrom.

The alumina sheet $SH_{200}$ and the zirconia sheet $SH_{100}$ are identical in thickness with each other (e.g., a thickness of 200 µm after fired). Grain size distributions and blend ratios of the compositions of the alumina sheet $SH_{200}$ and the zirconia sheet $SH_{100}$ are regulated to match shrinkage ratios thereof with each other when they are fired.

The zirconia sheet $SH_{100}$ is punched into a size and shape (e.g., a rectangular shape) identical with those of the through hole 201 formed in the alumina sheet $SH_{200}$. The punched out portion of the zirconia sheet $SH_{100}$ is embedded in the hole 201.

How to embed the punched out portion of the zirconia sheet $SH_{100}$ in the hole 201 of the alumina sheet $SH_{200}$ will be described below in detail with reference to FIGS. 3(a-1) to 3(d-2).

The zirconia sheet $SH_{100}$ and the alumina sheet $SH_{200}$ are, as illustrated in FIGS. 3(a-1) and 3(a-2), overlaid on each other and then placed in a punch press equipped with an upper die $D_{UP}$, an upper punch $P_{UP}$, a lower die $D_{LO}$, a lower punch $P_{LO}$, and a base BS.

The upper die $D_{UP}$ is, as illustrated in FIGS. 3(b-1) and 3(b-2), moved downward to punch the hole 201 in the alumina sheet $SH_{200}$ and, at the same time, punch out a portion of the zirconia sheet $SH_{100}$ into the shape contoured to conform with the hole 201. The punched portion of the zirconia sheet $SH_{200}$ will be the solid electrolyte body 100 after being fired. When the upper die $D_{UP}$ is further moved downward, the punched out portion of the zirconia sheet $SH_{100}$ is pressed by the lower punch $P_{LO}$ into the hole 201.

The piece $WST_{200}$ of material cut from the alumina sheet $SH_{200}$ to make the hole 201 is lifted up against the upper punch $P_{UP}$ pushed downward by an upper spring $SP_{UP}$ and ejected into the upper die $D_{UP}$.

A remaining frame-like portion of the zirconia sheet $SH_{100}$ pushes the lower die $D_{LO}$ downward against a lower spring $SP_{LO}$.

Afterward, the upper die $D_{UP}$ is, as illustrated in FIGS. 3(c-1) and 3(c-2), moved upward, the remaining frame-like portion of the zirconia sheet $SH_{100}$ from which the portion of the zirconia sheet $SH_{100}$ which has been embedded in the alumina sheet $SH_{200}$ and will be the solid electrolyte body 100 is cut is lifted up by the lower die $D_{LO}$. The piece $WST_{200}$ of material which is cut from the alumina sheet $SH_{200}$ and forced into the upper die $D_{UP}$ is ejected by the downward moving upper punch $P_{UP}$ out of the upper die $D_{UP}$.

In the manner, as described above, a solid electrolyte body/alumina sheet 20' that is an assembly of the alumina sheet $SH_{200}$ and the punched out portion of the zirconia sheet $SH_{100}$ which, after being fired, becomes the sensor/heater laminate sheet 20 is, as illustrated in FIGS. 3(d-1) and 3(d-2), produced.

The punch press that is, as can be seen from FIGS. 3(a-1) to 3(d-1), simple in structure is used to press the alumina sheet $SH_{200}$ and the zirconia sheet $SH_{100}$ overlaid on each other to make the hole 201 in the alumina sheet $SH_{200}$ and embed the punched out portion of the zirconia sheet $SH_{100}$ in the hole 201 simultaneously to make the solid electrolyte body/alumina sheet 20'. However, a zirconia sheet which, after being fired, becomes the solid electrolyte body 100 may be molded in the hole 201 of the alumina sheet $SH_{200}$ by putting a zirconia slurry in the hole 201 and volatilizing organic solvent therefrom to make the solid electrolyte body/alumina sheet 20'.

After dried, the zirconia sheet molded in the hole 201, however, usually shrinks, so that a central portion thereof is thinned. It is, therefore, essential to make the zirconia sheet whose central thickness is greater than the thickness of the rest using the surface tension of the zirconia slurry so that the thickness of the zirconia sheet after being fired will be constant.

The solid electrolyte body/alumina sheet 20' may alternatively be made by preparing a rectangular zirconia sheet which is similar in shape to the hole 201, but slightly smaller in size than the hole 201, putting it the hole 201, and loading a mixture of a zirconia slurry and an alumina slurry which is diluted by organic solvent into a clearance between the hole 201 and the zirconia sheet put in the hole 201 as an adhesive agent.

Figure 5A:
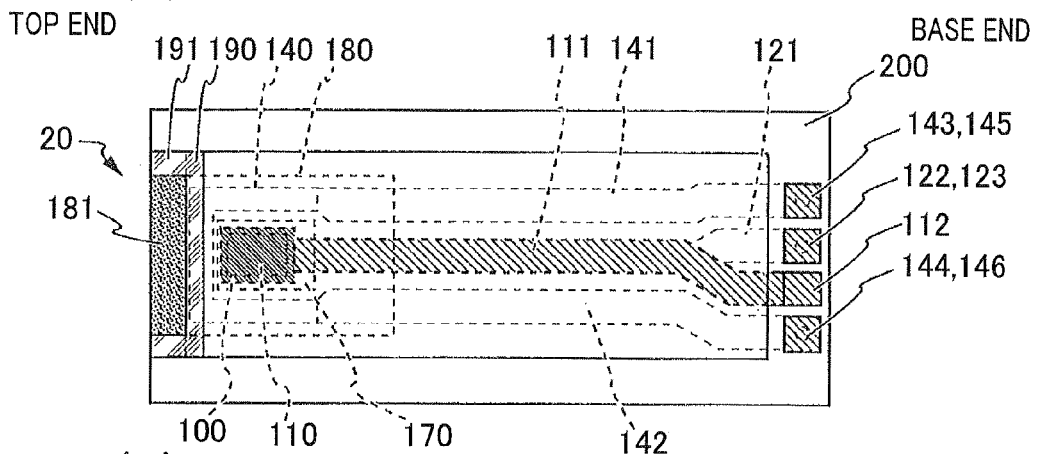
FIG. 5($a$) is a plane view which illustrates a surface of an insulating ceramic base of the gas sensor element of FIGS. 1($a$) to 1($d$) on which a measuring electrode is disposed.
Figure 5B:
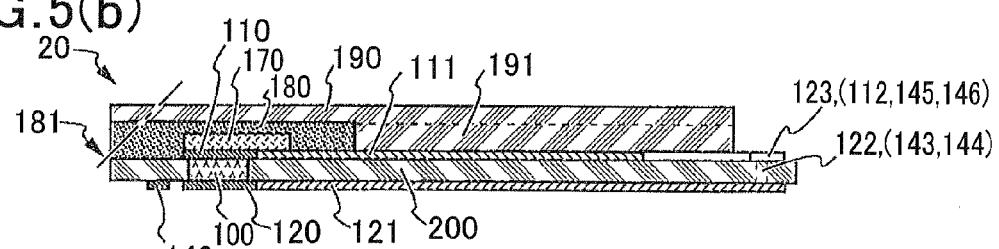
Figure 5C:
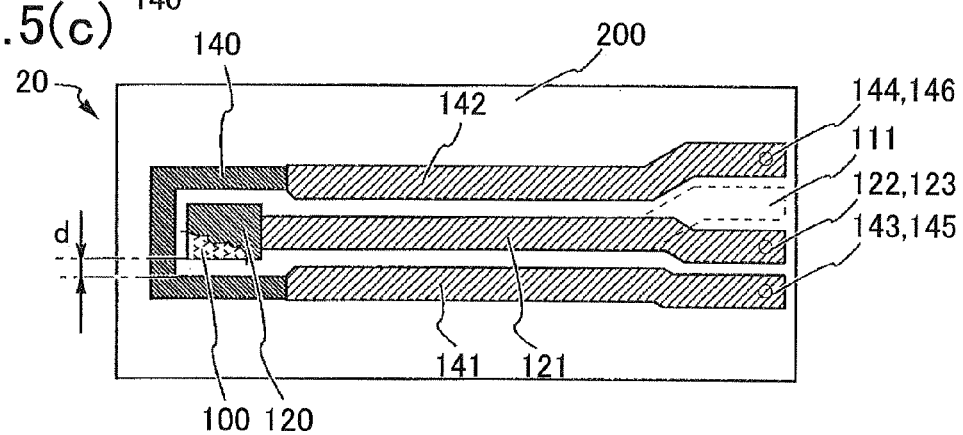
Figure 5D:
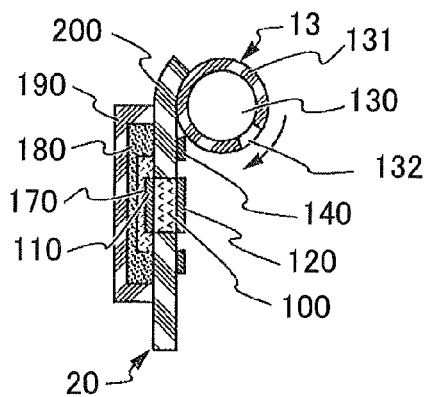

After the solid electrolyte body/alumina sheet 20' is produced in the manner, as described above, the measuring electrode 110, the measuring electrode lead 111, the measuring electrode terminal 112, the reference electrode 120, the reference electrode lead 121, the reference electrode via-conductor 122, the reference electrode terminal 123, the heating element 140, the heat leads 141 and 142, the heater via-conductors 143 and 144, the power supply terminals 145 and 146, the measurement gas chamber 170, the diffusion resistance layer 180, the shield layer 190, and the buffer layer 191 are, as illustrated in FIGS. 4 and 5(d), formed on the solid electrolyte body/alumina sheet 20' using, for example, known thick film printing techniques to make the sensor/heater laminate sheet 20.

The measuring electrode 110, the measuring electrode lead 111, the measuring electrode terminal 112, the reference electrode 120, the reference electrode lead 121, the reference electrode via-conductor 122, the reference electrode terminal 123, the heat leads 141 and 142, the heater via-conductors 143 and 144, the power supply terminals 145 and 146 may be made from a known conductive material such as gold, platinum, rhodium, palladium, ruthenium, or an alloy thereof. The conductive material may contain zirconia that is a main component of the solid electrolyte body 100 or alumina that is a main component of the insulating ceramic base 200.

The heating element 140 may be made from a resistance heating material such as platinum, rhodium, tungsten, rhenium, or an alloy thereof. The resistance heating material may contain alumina that is the main component of the insulating ceramic base 200.

The measuring electrode 110 is, as illustrated in FIGS. 4, 5(a), and 5(b), of a substantially rectangular shape and printed over the whole of one of the major surfaces of the solid electrolyte body 100.

The measuring electrode lead 111 is joined to one of ends of the measuring electrode 110 which faces the base end of the gas sensor element 10 and extends in a lengthwise direction of the insulating ceramic base 200 (i.e., the gas sensor element 10). The measuring electrode lead 111 is printed on one of the major surfaces of the insulating ceramic base 200 which lies flush with the measuring electrode 110.

The reference electrode 120 is, as illustrated in FIGS. 4, 5(b), and 5(c), of a substantially rectangular shape and printed over the whole of the other major surface of the solid electrolyte body 100. In other words, the reference electrode 120, the solid electrolyte body 100, and the measuring electrode 110 are laid to overlap each other in a thickness direction thereof.

The reference electrode lead 121 is joined to one of ends of the reference electrode 120 which faces the base end of the gas sensor element 10 and extends in the lengthwise direction of the insulating ceramic base 200 (i.e., the gas sensor element 10). The measuring electrode lead 111 is printed on one of the major surfaces of the insulating ceramic base 200 which lies flush with the reference electrode 120.

The via-conductor 122 is formed inside the hole 203 of the insulating ceramic base 200 using known vacuum printing techniques. The hole 203 extends through the opposed major surfaces of the insulating ceramic base 200 on which the measuring electrode 110 and the reference electrode 120 are disposed, respectively. The via-conductor 122 is electrically coupled to a base end of the reference electrode lead 121.

The reference electrode terminal 123 is printed on the major surface of the insulating ceramic base 200 which is flush with the measuring electrode 110. The reference electrode terminal 123 is joined electrically to the via-conductor 122.

The surface of the insulating ceramic base 200 which is on the same side as the surface of the solid electrolyte body 100 on which the measuring electrode 110 is disposed will also be referred to as a measuring electrode-side surface below. Similarly, the surface of the insulating ceramic base 200 which is on the same side as the surface of the solid electrolyte body 100 on which the reference electrode 120 is disposed will also be referred to as a reference electrode-side surface below. On the reference electrode-side surface, the heating element 140 is, as clearly illustrated in FIG. 5(c), printed. The heating element 140 is made of a substantially C-shaped conductor which embraces at least three of four sides of the reference electrode 120 at a constant interval d away from the solid electrolyte body 100 and/or the reference electrode 120. The interval d is longer than or equal to 0.1 mm or shorter than or equal to 3 mm.

The heater leads 141 and 142 are printed on the reference electrode-side surface of the insulating ceramic base 200 in electric connection with the ends of the heating element 140.

The via-conductors 143 and 144 are formed inside the holes 202 and 204 of the insulating ceramic base 200 using the known vacuum printing techniques. The holes 202 and 204 extend through the measuring electrode-side surface and the reference electrode-side surface of the insulating ceramic base 200. The via-conductors 143 and 144 are electrically coupled to base ends of the heater leads 141 and 142, respectively.

The heater terminals 145 and 146 (which are also referred to as power supply terminals) are printed on a base end portion of the measuring electrode-side surface of the insulating ceramic base 200. The heater terminals 145 and 146 are joined electrically to the via-conductors 143 and 144, respectively.

The measurement gas chamber 170 is, as illustrated in FIGS. 4, 5(b), and 5(d), of a substantially rectangular shape and covers the whole of the surface of the measuring electrode 110. The measurement gas chamber 170 is formed by applying a paste made of a mixture of binding agent and organic solvent over the measuring electrode 110 and burning it out when the sensor/heater laminate sheet 20 is fired in the manner, as described later.

The diffusion resistance layer 180 is made from a diffusion layer-making paste which, after fired, becomes a porous layer. The diffusion layer-making paste is made by blending alumina powder, resin powder, and binder with each other and mixing organic solvent with it. The ratio of such compositions is so selected that the porous layer has a given degree of diffusion resistance. The diffusion layer-making paste is printed over the whole of the surface of the measurement gas chamber 170 so that it extends until an edge of the top end (i.e., a left end, as viewed in FIG. 4) of the insulating ceramic base 200.

The end of the diffusion resistance layer 180 is, as illustrated in FIGS. 4, 5(a), and 5(b), cut or grounded to form a tapered surface (i.e., the slant measurement gas inlet surface 181) which is not covered with the shield layer 190 and through which the measurement gas is to be introduced into the diffusion resistance layer 180.

The slant measurement gas inlet surface 181 is inclined at a given angle to the length of the gas sensor element 10 to define an inlet opening which facilitates the ease with which a flow of the measurement gas moving substantially perpendicular to the length of the gas sensor element 10 is admitted into the diffusion resistance layer 180 and then into the measurement gas chamber 170 which is lower in diffusion resistance than the diffusion resistance layer 180.

The slant measurement gas inlet surface 181 may be formed either before or after the sensor/heater laminate sheet 20 is wrapped about the cylindrical ceramic base 13 or after an assembly of the sensor/heater laminate sheet 20 and the cylindrical ceramic base 13 is fired.

The shield layer 190 is, as illustrated in FIGS. 4, 5(a), and 5(b), printed using an insulating paste such as alumina over the diffusion resistance layer 180 and the buffer layer 191. The shield layer 190 does not cover the terminals 145, 112, 123, and 146. The buffer layer 191 is printed using an insulating paste such as alumina on the measurement electrode-side surface of the insulating ceramic layer 200 in alignment with the diffusion resistance layer 180 in the lengthwise direction of the gas sensor element 10.

The shield layer 190 may be made using the alumina sheet $SH_{200}$.

In the manner, as described above, the planar sensor/heater laminate sheet 20 is produced which is a stack of the solid electrolyte body 100, the measuring electrode 110, the reference electrode 120, the heating element 140, the measurement gas chamber 170, the diffusion resistance layer 180, the shield layer 190, the insulating ceramic layer 200, etc.

The cylindrical ceramic base 13 is formed by a hollow ceramic cylinder made of an insulating ceramic material such as alumina. The hollow ceramic cylinder may be made using known extrusion-molding, injection-molding, CIP (Cold Isostatic Pressing), or HIP (Hot Isostatic pressing) techniques. The cylindrical ceramic base 13 may be shaped to be 2.5 mm in outer diameter, 2.1 mm in inner diameter, and 50 mm in length. The cylindrical ceramic base 13 has the closed end 133 that is the top end of the gas sensor element 10 and the open end 134 that is to face the base end of the gas sensor 1. The cylindrical ceramic base 13 has defined therein the cylindrical reference gas chamber 130 to which the air is admitted as the reference gas. The cylindrical ceramic base 13 also has a rectangular hole or window 132 which passes through the side wall 131. The window 132 is located closer to the closed end than to the open end 134.

The production of the cylindrical ceramic base 13 using the extrusion process is achieved by blending alumina power with binder, parting agent (also called mold release agent), and deionized water to produce a green body, extruding the green body into a hollow ceramic cylinder, cutting the hollow ceramic cylinder into a given length, closing one of open ends of the hollow ceramic cylinder using a similar green body, drying the hollow ceramic cylinder to have an increased mechanical strength, and drilling the side window 132.

The production of the cylindrical ceramic base 13 using the injection, the CIP, or the HIP process is achieved by using a set of dies and a core. The use of the dies and the core enables the reference gas chamber 130, the side wall 131, the side window 132, and the closed end 133 to be formed simultaneously.

After the sensor/heater laminate sheet 20 and the cylindrical ceramic base 13 are produced in the manner, as described above, the sensor/heater laminate sheet 20 is, as illustrated in FIG. 5(d), twisted or wrapped around the peripheral wall of the cylindrical ceramic base 13 and then fired at a given temperature. For example, such an assembly is heated at 400 degree C. (Celsius, centigrade) for four hours in the atmosphere to be degreased and then fired at approximately 1500 degree C. for two hours to complete the gas sensor element 10.

When the sensor/heater laminate sheet 20 is wrapped about the cylindrical ceramic base 13, the reference electrode 110 is, as can be seen from FIG. 1(c), positioned in coincidence with the side window 132 of the cylindrical ceramic base 13 in the radius direction thereof.

In the ceramic base wrapping process, it is advisable that a bonding paste be applied to the reference electrode-side surface of the insulating ceramic base 200 except the reference electrode 120 to glue the sensor/heater laminate sheet 20 to the cylindrical ceramic base 200. The bonding paste may be made by dispersing alumina and binder in organic solvent.

The wrapping of the sensor/heater laminate sheet 20 around the cylindrical ceramic base 13 may be achieved after the cylindrical ceramic base 13 is dried, after the binder is removed from the cylindrical ceramic base 13, or after the cylindrical ceramic base 13 is fired temporarily or completely. The drying of the cylindrical ceramic base 13 results in an increase in mechanical strength, thus facilitating the ease with which the sensor/heater laminate sheet 20 is wrapped about the cylindrical ceramic base 13.

After the binder is removed from the cylindrical ceramic base 13, the cylindrical ceramic base 13 become porous and thus is impregnated with the bonding paste, thereby resulting in a firm joint of the cylindrical ceramic base 13 to the sensor/heater laminate sheet 20. This minimizes the risk of delamination of the cylindrical ceramic base 13 and the sensor/heater laminate sheet 20.

When the cylindrical ceramic base 13 is fired temporarily at a temperature lower than that at which the assembly of the cylindrical ceramic base 13 and the sensor/heater laminate sheet 20 is fired, it will cause neck growth between alumina particles in the cylindrical ceramic base 13, thereby resulting in an increase in mechanical strength of the cylindrical ceramic base 13. This minimizes the probability of breakage of the cylindrical ceramic base 13 around which the sensor/heater laminate sheet 20 is wrapped.

The firing of the cylindrical ceramic base 13 will result in an increase in mechanical strength thereof, thus facilitating the ease with which the sensor/heater laminate sheet 20 is wrapped about the cylindrical ceramic base 13.

The firing of the cylindrical ceramic base 13 will also result in a decrease in degree of shrinkage of the assembly of the cylindrical ceramic base 13 and the sensor/heater laminate sheet 20 when fired to complete the gas sensor element 10. The thermal stress acting on the sensor/heater laminate sheet 20 will, therefore, be small, thus reducing the probability of cracks in or delamination of the sensor/heater laminate sheet 20 from the cylindrical ceramic base 13. Care, however, should be taken not to over-fire the cylindrical ceramic base 13.

FIGS. 6(a) to 7(d) show modifications of the gas sensor element 10.

Figure 6A:
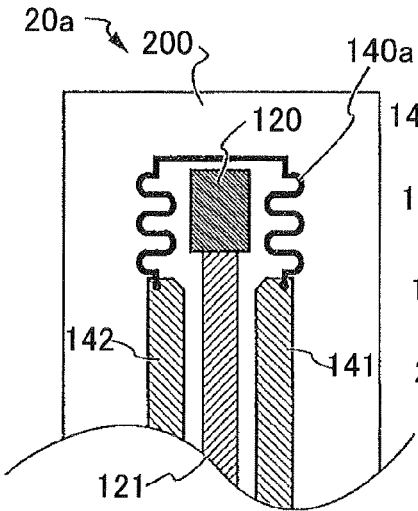
FIG. 6($a$) is a partially plane view which illustrates a surface of an insulating ceramic base of a modified form of a gas sensor element on which a heating element and a reference electrode are disposed.
Figure 6B:
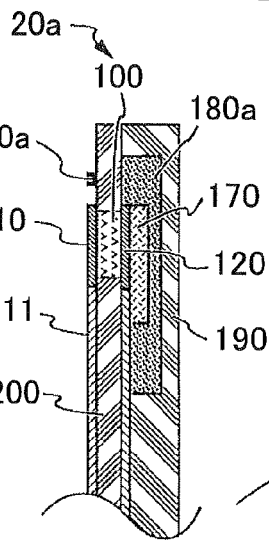
Figure 6C:
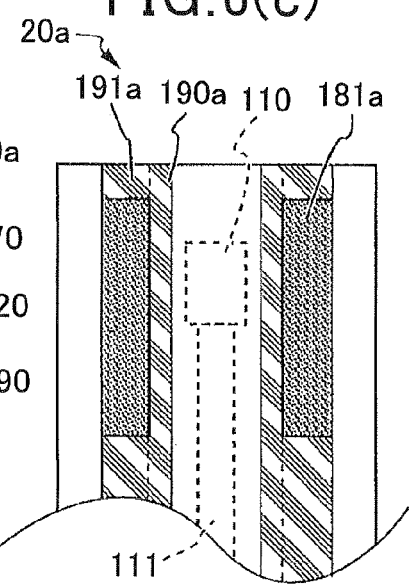
Figure 6D:
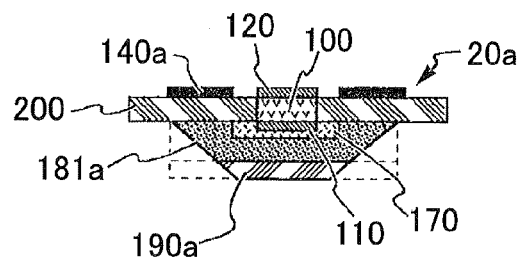
Figure 6E:
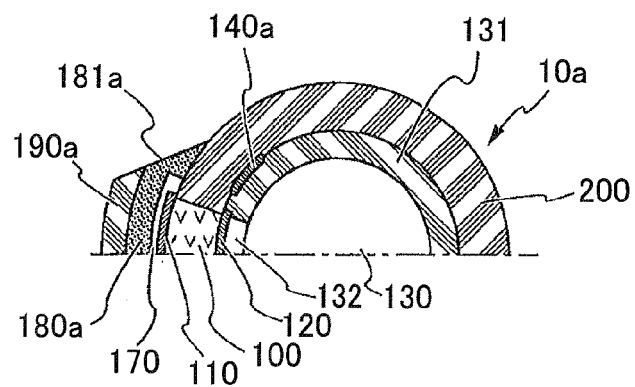

The heating element 140 is, as described above of a C-shape surrounding the reference electrode 120, but may be printed, as illustrated in FIG. 6(a), in the form of a bellows 140a.

The slant measurement gas inlet surface 181 of the diffusion resistance layer 180 serving as the gas inlet opening is defined by the tapered end surface thereof, but however, side surfaces of the diffusion resistance layer 180 may alternatively be, as illustrated in FIGS. 6(b), 6(c), 6(d), and 6(e), tapered to form gas inlet openings through which the measurement gas is admitted into the diffusion resistance layer 180. The tapered side surfaces extend in the lengthwise direction of the insulating ceramic base 200. The gas inlet openings are oriented substantially perpendicular to the length of the gas sensor element 10.

The measuring electrode terminal 112, the reference electrode terminal 123, and the heater terminals 145 and 146 are, as illustrated in FIG. 2, collected on an area of the surface of the insulating ceramic base 200 which occupies a portion of the circumference of the insulating ceramic base 200, is aligned with the sensing mechanism, in other words, the length of the diffusion resistance layer 180, and located closer to the base end of the cylindrical ceramic base 13 than to the top end thereof, but however, may be, as denoted by numerals 112b, 123b, 145b, and 146b in FIGS. 7(a) to 7(c), arrayed at regular or equi-intervals away from each other in the circumferential direction of the insulating ceramic base 200 (i.e., the cylindrical ceramic base 13) and located closer to the base end of the insulating ceramic base 200 than to the top end thereof. In this case, the terminals 112b, 123b, 145b, and 146b may be, as illustrated in FIGS. 7(c) and 7(d), connected to the power supply control circuit and the detector circuit, as described above, through substantially U-shaped spring connectors, as illustrated in FIG. 7(d). the spring connectors are equipped with sets of a contact 113b and a terminal 114b, a contact 124b and a terminal 125b, a contact 147b and a terminal 149b, a contact 148b and a terminal 150b, respectively. The contacts 113b, 124b, 147b and 148b are elastically placed in electric contact with the terminals 112b, 123b, 145b, and 146*b* on the insulating ceramic base 200, respectively. This structure facilitates the ease with which the gas sensor element 10 is installed in the gas sensor 1 and improves the stability in electric connection of the terminals 112*b*, 123*b*, 145*b*, and 146*b* to the contacts 113*b*, 124*b*, 147*b* and 148*b* against external mechanical vibration.

The heater terminals 145*b* and 146*b* are, as can be seen in FIG. 7(*c*), connected electrically to the power supply control circuit through the terminals 149*b* and 150*b* and conductive lines, respectively. The power supply control circuit works to control the supply of electric power to the heating element 140 and is equipped with a semiconductor switch SW such as a MOSFET, an SCR, or an IGBT and a driver DRV. The semiconductor switch SW works to selectively establish or block the supply of power from a storage battery BATT to the heater terminals 145*b* and 146*b*. The driver DRV works to control the operation of the semiconductor switch SW in a PWM control mode or a switching on/off control mode.

The measuring electrode 110 and the reference electrode 120 are electrically connected to the detector circuit DTC through the terminals 114*b* and 125*b* and conductive lines, respectively. The detector circuit DTC works as a gas concentration determining circuit to monitor a difference in electromotive force between the measuring electrode 110 and the reference electrode 120 or an electric current flowing between the measuring electrode 110 and the reference electrode 120 and determine the concentration of a specified component (e.g., $O_2$) contained in the measurement gas as a function of the monitored difference or current.

The disadvantages that gas sensor elements 10*z*, 10*g*, and 10*f* which are equipped with conventional structures and gas sensor elements 10*c*, 10*d*, and 10*e* which have technical limitations to beneficial effects as offered by the structure of the gas sensor element 10 will be described below with reference o FIGS. 8(*a*) to 13(*b*).

Figure 8A:
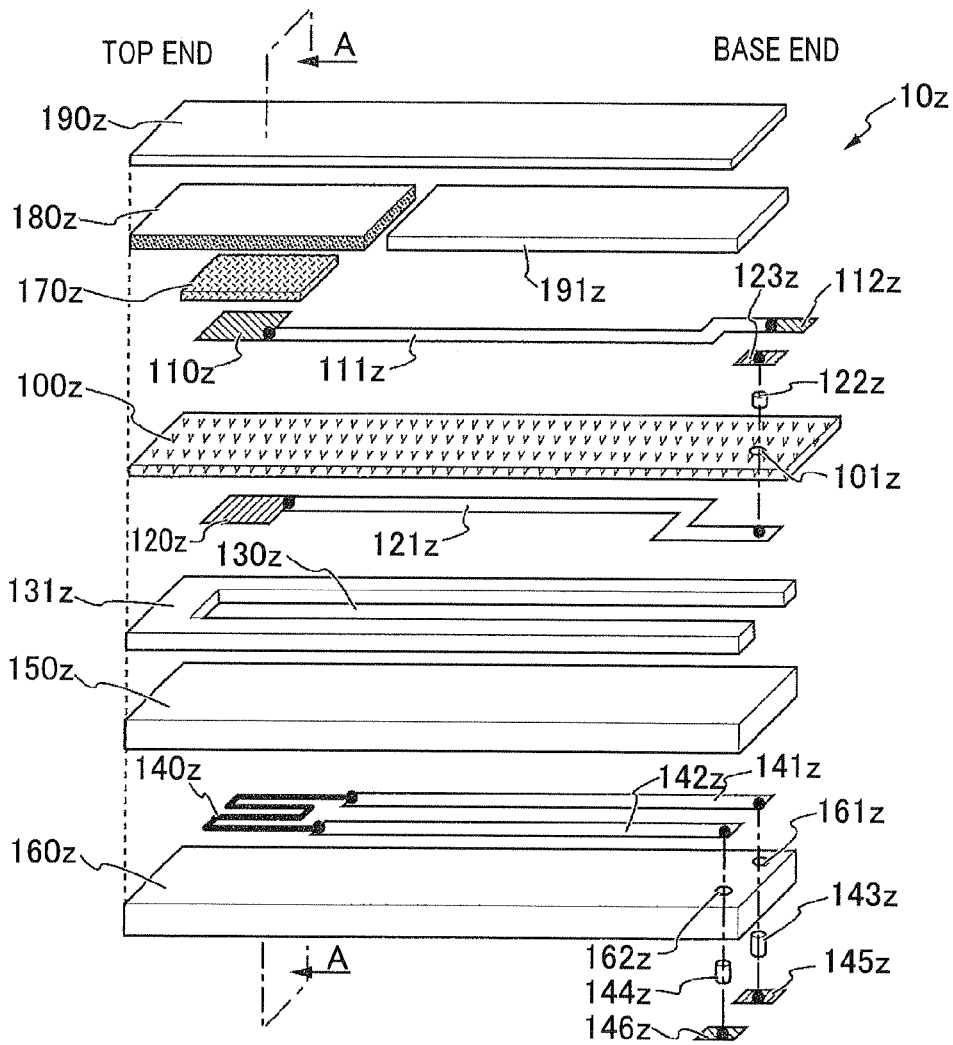
FIG. 8($a$) is an exploded perspective view which shows a comparative example No. 1 of a gas sensor element.
Figure 8B:
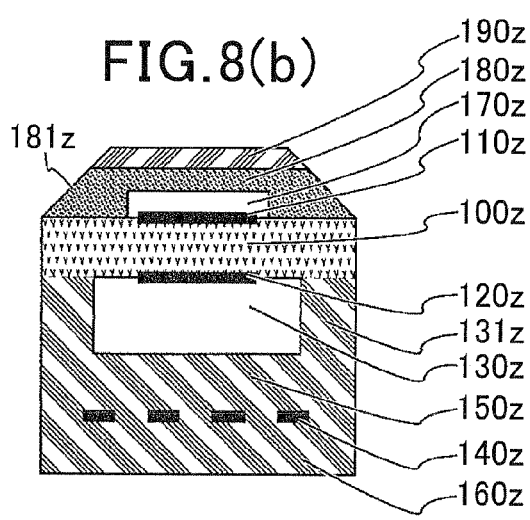
Figure 8C:
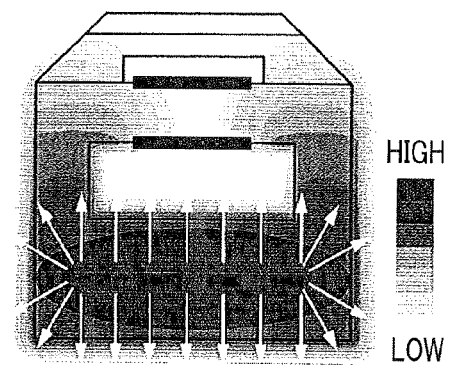

FIGS. 8(*a*), 8(*b*), and 8(*c*) illustrate, as a comparative example No 1, the gas sensor element 10*z* having a typical planar structure as taught in Japanese Patent First Publication No. H01-253649 discussed in the introductory part of this application.

In FIGS. 8(*a*) to 8(*c*), the same reference numbers with a suffix "z", as those employed above, refer to similar or same parts, and explanation thereof in detail will be omitted here.

The planar solid electrolyte body 100*z* has two opposed major surfaces. On one of the major surfaces, the measuring electrode 110*z*, the measuring electrode lead 111*z*, the measurement gas chamber 170*z*, the diffusion resistance layer 180*z*, the shield layer 190*z*, the buffer layer 191*z*, and the reference electrode terminal 123*z* are formed. On the other major surface, the reference electrode 120*z* and the reference electrode lead 121*z* are formed. The solid electrolyte body 100*z* has formed therein the hole 101*z* in which the via-conductor 122*z* is formed to connect between the end of the reference electrode lead 121*z* and the reference electrode terminal 123*z*.

The reference gas chamber layer 131*z* is stacked on the solid electrolyte body 100*z*. The planar insulating layer 150*z* is also stacked on the reference gas chamber layer 131*z* to define the reference gas chamber 130*z* along with the reference gas chamber layer 131*z*. The heater carrier layer 160*z* on which the heating element 140*z*, and the heater leads 141*z* 142*z* are formed is affixed to the insulating layer 150*z*. The heater carrier layer 160*z* has formed therein holes 161*z* and 162*z* in which via-conductors 144*z* and 143*z* are formed to connect the heater leads 141*z* and 142*z* and the heater terminals 145*z* and 146*z*, respectively.

The shield layer 181*z* has the slant measurement gas inlet surfaces 181*z* formed on the sides thereof.

When the heating element 140*z* is activated, thermal energy heat produced by the heating element 140*z*, as illustrated in FIG. 8(*c*), heats the air admitted into the reference gas chamber 130*z* through the insulating layer 150*z* and is also transmitted to the solid electrolyte body 100*z* through the air and the reference gas chamber layer 131*z*.

The air exists in the reference gas chamber 130*z* in the form of a layer. Such an air layer is high in thermal insulation and low in thermal conductivity (0.15 to 0.25 W/m·k).

The thermal energy produced by the heating element 140*z* is partially transmitted to the solid electrolyte body 100*z* through the insulating layer 150*z* made of alumina whose thermal conductivity is high (20 to 30 W/m·k) and the reference gas chamber layer 131*z*. The sensing mechanism made up of the measuring electrode 100*z*, the reference electrode 120*z*, etc. is, thus, heated by the thermal energy transmitted through the solid electrolyte body 100*z* which is made of zirconia whose thermal conductivity is low (2 to 3 W/m·k).

Most of the thermal energy produced by the heating element 140*z* is first consumed in heating the air in the reference gas chamber 130*z*. The air, as elevated in temperature thereof, is then transmitted to heat the solid electrolyte body 100*z*.

The radiant heat from the heating element 140*z* is also transmitted directly to the solid electrolyte body 100*z*. Yttria-stabilized zirconia which is typically used as material of the solid electrolyte body 100*z* is white in color and thus reflects most of the radiant heat. The thermal energy produced by the heating element 140 is, therefore, not used in activating the solid electrolyte body 100*z* immediately after the heating element 140 is energized, thus resulting in a delay in bringing the gas sensor element 10*z* into a condition to measure the concentration of gas correctly.

The heating element 140*z* is, as described above, interposed between the insulating layer 150*z* and the heater carrier layer 160*z* to make a heating mechanism. The sensing mechanism (i.e., the solid electrolyte body 100*z*, the measuring electrode 110*z*, the reference electrode 120*z*, and the reference gas chamber 130*z*) and the heating mechanism (i.e., the heating element 140*z*, the insulating layer 150*z*, and the heater carrier layer 160*z*) are on opposite sides of the reference gas chamber 130*z*. The temperature of the heating mechanism is, thus, elevated more than that of the sensing mechanism. This will cause the heating mechanism to be greater in degree of thermal expansion than the sensing mechanism, thus resulting in tensile stress acting on the outer surface of the heating mechanism, which may lead to cracks in the insulating layer 150*z* and the heater carrier layer 160*z*.

In order to minimize the risk of such cracks, the insulating layer 150*z* and the heater carrier layer 160*z* may be thickened to absorb the thermal stress, but it results in an increase in overall size of the gas sensor element 10*z*, in other words, an increase in volume of the gas sensor element 10*z* to be heated. This also results in a delay in activating the gas sensor element 10*z*.

The solid electrolyte body 100*z* is, as illustrated in FIG. 8(*a*), entirely planar and has the electric conductivity. The measuring electrode lead 111*z*, the reference electrode lead 121*z*, the measuring electrode terminal 112*z*, the via-conductor 122*z*, and the reference electrode terminal 123*z* are formed on the solid electrolyte body 100*z*. Application of voltage between the measuring electrode terminal 112*z* and the reference electrode terminal 123*z*, therefore, causes electric current to flow through the solid electrolyte body 100*z*, which results in a decrease in accuracy in measuring the concentration of gas.

FIGS. 9(*a*), 9(*b*), and 9(*c*) illustrate, as a comparative example No 2, the gas sensor element 10*g* which is similar in structure to the one, as taught in Japanese Patent First Publication No. H01-253649 discussed in the introductory part of this application.

In FIGS. 9(*a*) to 9(*c*), the same reference numbers with or without a suffix "g", as those employed above, refer to similar or same parts, and explanation thereof in detail will be omitted here.

The solid electrolyte body 100 of the gas sensor element 10 of the embodiment is, as illustrated in FIG. 4, embedded in the insulating ceramic base 200, while the solid electrolyte body 100*g* of the gas sensor element 10*g* is planer and wrapped directly about the cylindrical insulating base 13. Specifically, the solid electrolyte body 100*g* has affixed on opposed major surfaces thereof the measuring electrode 110*g*, the measuring electrode lead 111*g*, the measuring electrode terminal 112*g*, the reference electrode 120*g*, the reference electrode lead 121*g*, the via-conductor 122*g*, and the reference electrode terminal 123*g*. The solid electrolyte body 100*g* is wrapped around the cylindrical insulating base 13*b* with the reference electrode 120*g* facing the hole 132*g*. The heating element 140*g*, the heater leads 141*g* and 142*g*, and the heater terminals 145*g* and 146*g* are disposed through the insulating layer 150*g* on an area of the solid electrolyte body 100 around the measuring electrode 110*g*. The opening 151*g* is formed in a portion of the insulating layer 150 which coincides with the measuring electrode 110*g*. The opening 151*g* defines, as illustrated in FIG. 9(*b*), the measurement gas chamber 170*g*. The diffusion resistance layer 180*g* is disposed on the insulating layer 150*g* to cover the measuring electrode 110*g* exposed to the opening 151*g*. The shield layer 190*g* is laid over the diffusion resistance layer 180*g*. These arrangements enables the interval (i.e., the insulating interval d) between the measuring electrode 100*g* and the inner edge of the heating element 140 to be shortened to accelerate the activation of the solid electrolyte body 100*g*, but ensuring a desired degree of electric insulation between the heating element 140*g* and the solid electrolyte body 100*g* requires an increase in thickness $t_{150}$ of the insulating layer 150*g* to set the insulating interval d to be greater than or equal to, for example, 100 μm.

The solid electrolyte body 100*g* is wrapped around the whole circumference of the cylindrical ceramic base 13. In other words, the insulating layer 150*g* is wrapped around the whole of the circumference of the cylindrical ceramic base 13. The shield layer 190*g* covers the whole of the circumference of the insulating layer 150*g*. The slant measurement gas inlet surface 181*g* is, thus, formed inevitably on the top end of the diffusion resistance layer 180*g*.

The outer diameter of the gas sensor element 10*g* is, therefore, increased, thereby resulting in an increase in entire thermal capacity of the gas sensor element 10*g*.

The heating element 140*g*, as can be seen from FIG. 9(*c*), heats the solid electrolyte body 100*g* from the outside in the circumferential direction of the solid electrolyte body 100*g*. The thermal energy produced by the heating element 140*g*, therefore, like in the comparative example No. 1, passes through the solid electrolyte body 100*g* which is low in thermal conductivity and then reaches two sides of the sensing mechanism.

The heating element 140*g* is located close to the outer periphery of the gas sensor element 10*g*, so that lots of thermal energy diffuses to the measurement gas around the gas sensor element 10*g*, thus resulting in lack of the thermal energy to heat the air in the reference gas chamber 130.

The structure of the comparative example No. 2 is, therefore, low in energy efficiency and takes time to activate the sensing mechanism completely.

Figure 10A:
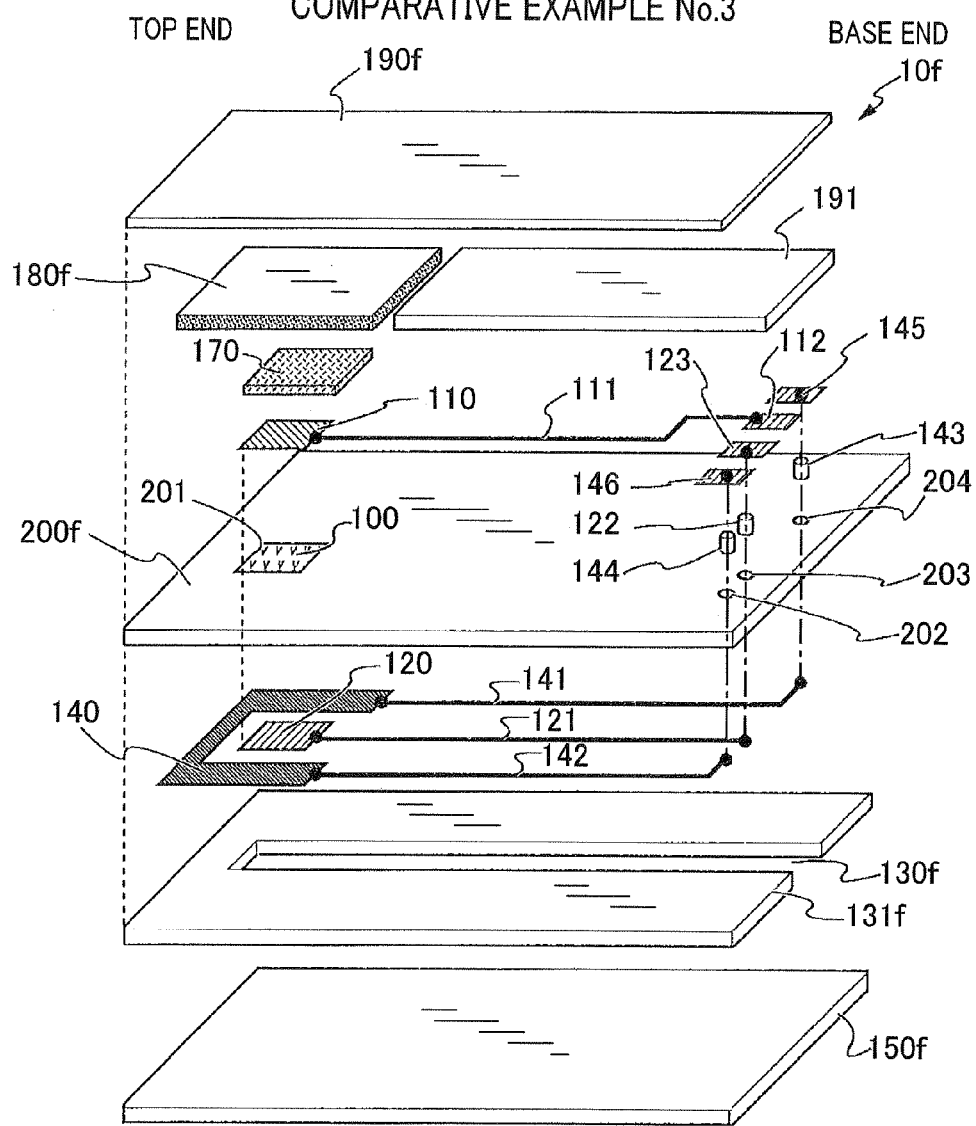
FIG. 10(a) is an exploded perspective view which shows a comparative example No. 3 of a gas sensor element.
Figure 10B:
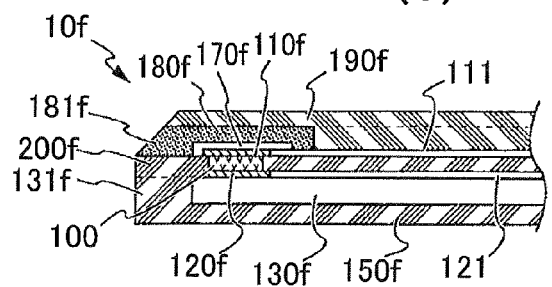
FIG. 10(b) is a partially longitudinal sectional view of the gas sensor element of FIG. 10(a)
Figure 10C:
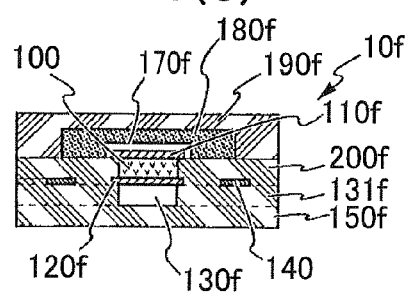
FIG. 10(c) is a transverse sectional view of the gas sensor element of FIG. 10(a)

FIGS. 10(*a*), 10(*b*), and 10(*c*) illustrate, as a comparative example No 3, the gas sensor element 10*f*. In FIGS. 10(*a*) to 10(*c*), the same reference numbers with or without a suffix "f", as those employed above, refer to similar or same parts, and explanation thereof in detail will be omitted here.

The gas sensor element 10*f* is similar to the gas sensor element 10 in that the solid electrolyte body 100 is embedded in the insulating ceramic base 200*f*, and the heating element 140*f* is located on the surface of the insulating ceramic base 200*f* on which the reference electrode 120 is disposed, but however, the reference gas chamber 130*f* is defined by a stack of the C-shaped reference gas chamber layer 131*f* and the planar insulating layer 150*f* without use of the cylindrical ceramic base 13.

Accordingly, the gas sensor element 10*f* is, as can be seen in FIG. 10(*b*), identical in longitudinal section with the gas sensor element 10, but different, as can be seen in FIG. 10(*c*), in transverse section from the gas sensor element 10. Quick thermal activation of the solid electrolyte body 100 is, therefore, thought of as being achieved, like the gas sensor element 10, through the insulating ceramic base 200*f* which is high in thermal conductivity by mounting the heating element 140 on the same side of the insulating ceramic base 200*f* as the reference electrode 120.

However, because the heating element 140 extends outside the sides of the reference electrode 120*f* on the insulating ceramic base 200*f* which is planar, the gas sensor element 10*f* has an increased width. This results in increased sensitivity of the gas sensor element 10*f* to thermal stress arising from, for example, splashing with water, which decreases the durability of the gas sensor element 10*f*.

Figure 11A:
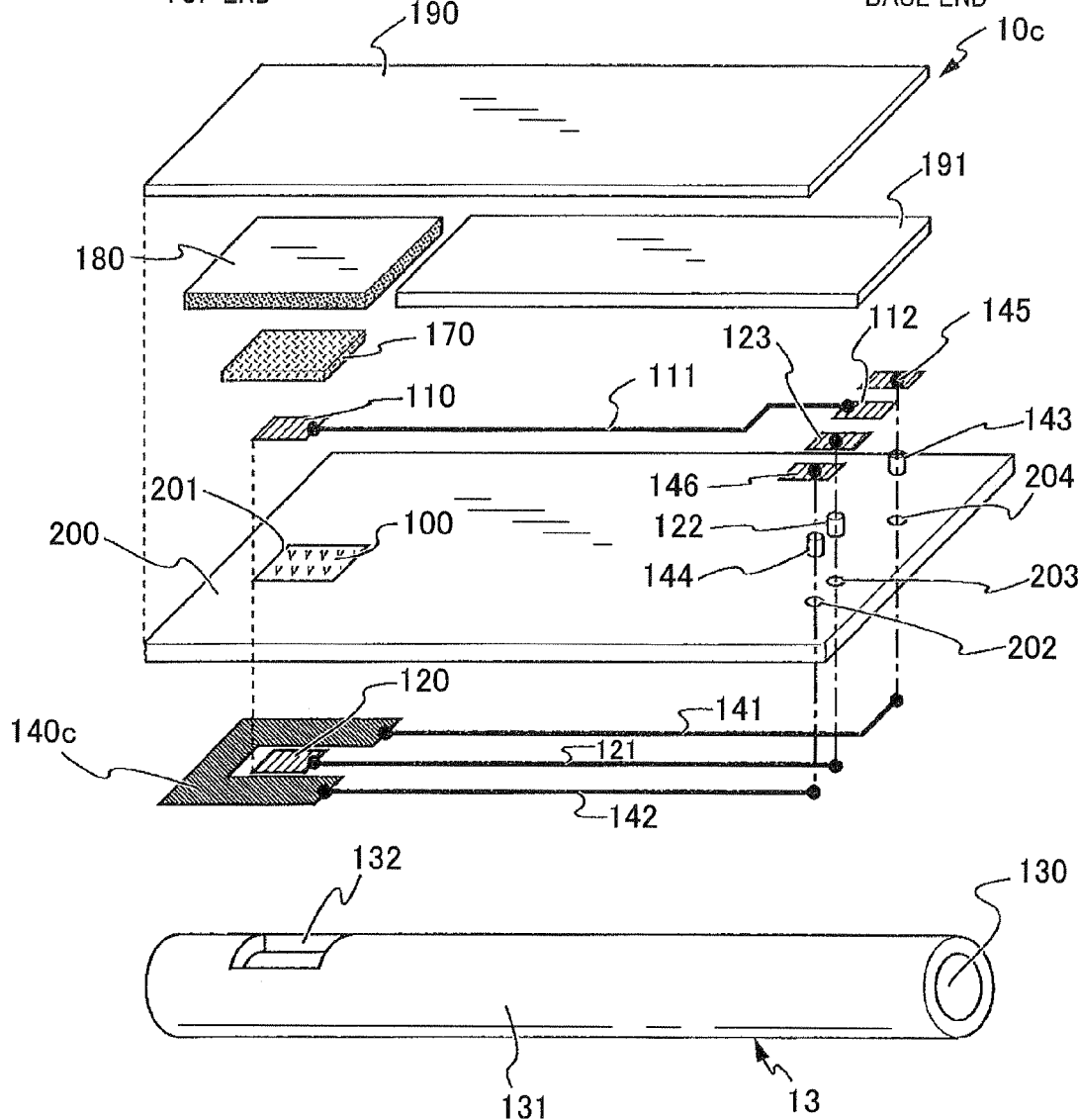
FIG. 11(a) is an exploded perspective view which shows a comparative example No. 4 of a gas sensor element.
Figure 11B:
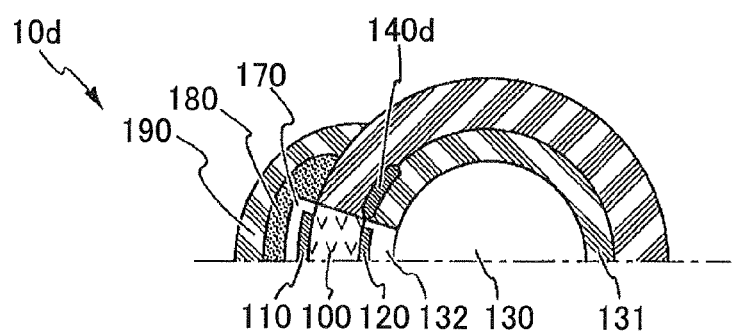
FIG. 11(b) is a partially transverse sectional view of the gas sensor element of FIG. 11(a)

FIGS. 11(*a*), 11(*b*), and 11(*c*) illustrate, as a comparative example No 4, the gas sensor element 10*c*. In FIGS. 11(*a*) to 11(*c*), the same reference numbers with or without an suffix "c", as those employed above, refer to similar or same parts, and explanation thereof in detail will be omitted here.

The gas sensor element 10*f* is different from the gas sensor element 10 of FIG. 1 only in that the insulating interval d between the edge of the solid electrolyte body 100 and the heating element 140*c* is shorter than 0.1 mm that is a lower limit of a set range of the insulating interval d in the gas sensor element 10.

The structure of the gas sensor element 10*c* is identical in effect to activate the sensing mechanism quickly with that of the gas sensor element 10, but the decreased insulating interval d results in leakage of current from the heating element 140*c* when energized, which leads to instability in operation of the gas sensor element 10*c*.

Figure 12A:
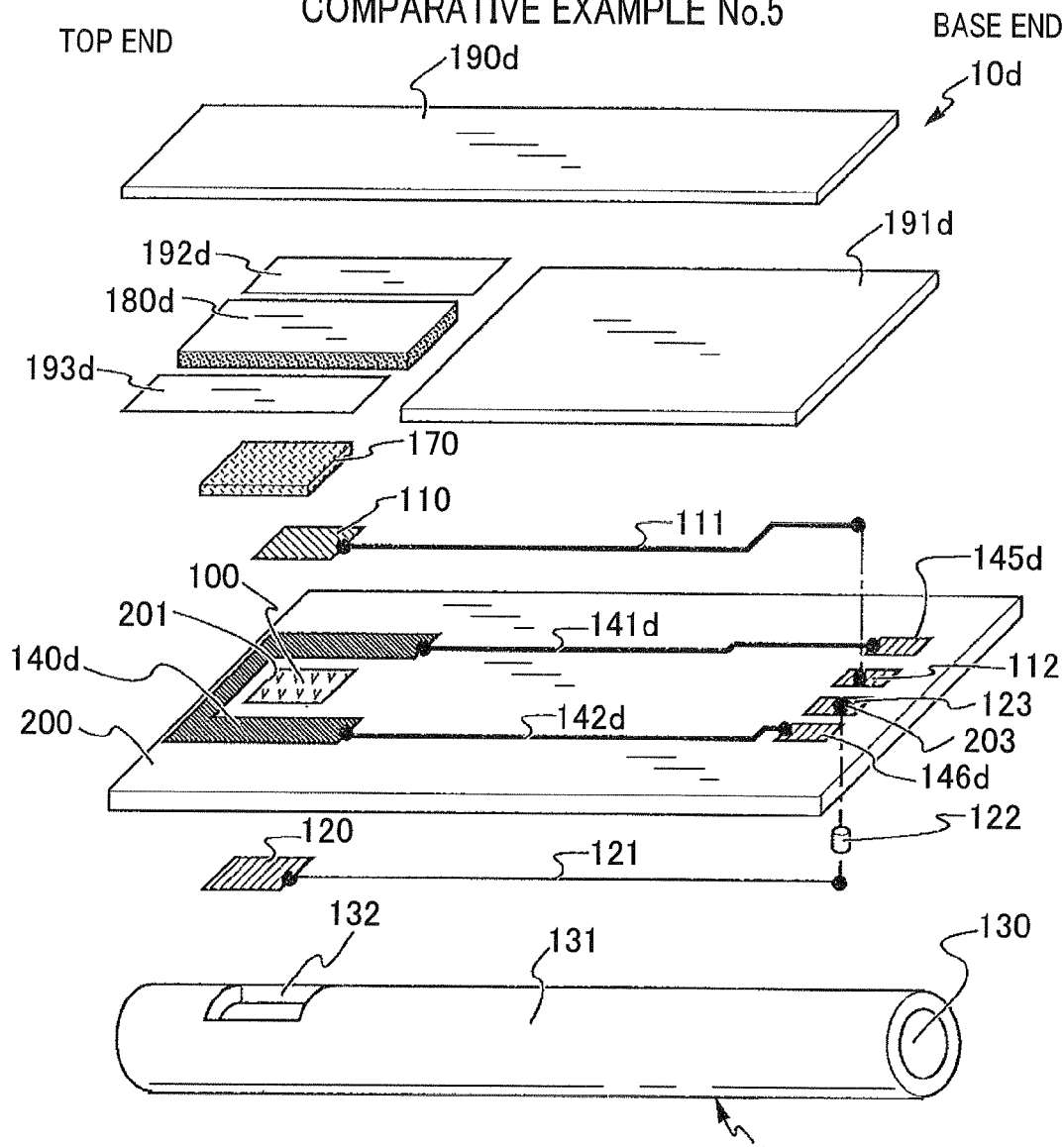
FIG. 12(a) is an exploded perspective view which shows a comparative example No. 5 of a gas sensor element.
Figure 12B:
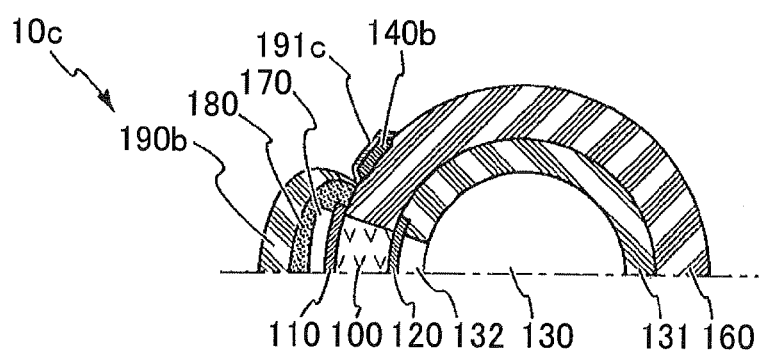
FIG. 12(b) is a partially transverse sectional view of the gas sensor element of FIG. 12(a)

FIGS. 12(*a*), 12(*b*), and 12(*c*) illustrate, as a comparative example No 5, the gas sensor element 10*d*. In FIGS. 12(*a*) to 12(*c*), the same reference numbers with or without an suffix "d", as those employed above, refer to similar or same parts, and explanation thereof in detail will be omitted here.

The structure of the gas sensor element 10*d* is similar to that of the gas sensor element 10 of FIG. 1 in that the solid electrolyte body 100 is embedded in the insulating ceramic base 200 with the measuring electrode 110 and the reference electrode 120 affixed to opposed major surfaces thereof and wrapped around the cylindrical ceramic base 13, but different in that the heating element 140*d* is disposed on the surface of the insulating ceramic base 200 which is on the same side as the measuring electrode 110, and the insulating layers 192*d* and 193*d* are printed over the heating element 140*d* as protective layers which isolate the heating element 140d from the measurement gas. The insulating layers 192d and 193d are 20 µm in thickness.

The quick thermal activation of the solid electrolyte body 100 is, therefore, thought of as being achieved by shortening the insulating interval between the measuring electrode 110 and the heating element 140d, but the insulating layers 192d and 193d printed to cover the heating element 140d are thin, thus resulting in greater concern about the deterioration of operation of the heating element 140d due to exposure to poisons in the measurement gas, as having penetrated pinholes in the insulating layers 192d and 193d.

The heating element 140d is, like in the comparative example No. 2, located close to the outer periphery of the gas sensor element 10d, so that lots of thermal energy produced by the heating element 140d diffuses to the measurement gas around the gas sensor element 10d, thus resulting in lack of the thermal energy to heat the air in the reference gas chamber 130.

Figure 13A:
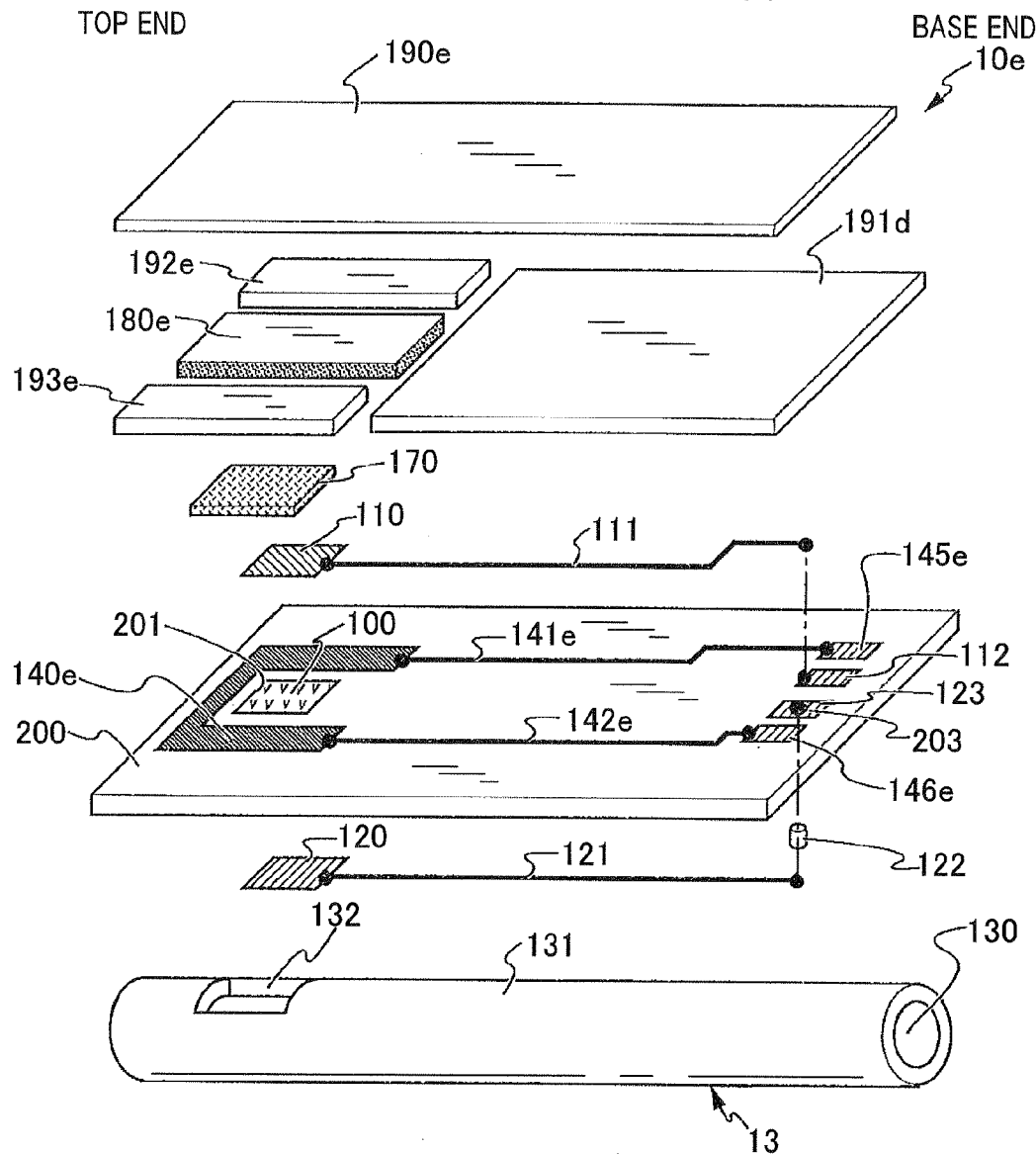
FIG. 13(a) is an exploded perspective view which shows a comparative example No. 6 of a gas sensor element.
Figure 13B:
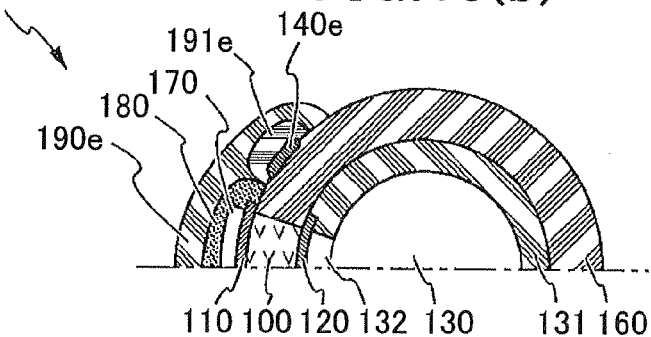
FIG. 13(b) is a partially transverse sectional view of the gas sensor element of FIG. 13(a)

FIGS. 13(a), 13(b), and 13(c) illustrate, as a comparative example No 6, the gas sensor element 10e. In FIGS. 13(a) to 13(c), the same reference numbers with or without a suffix "e", as those employed above, refer to similar or same parts, and explanation thereof in detail will be omitted here.

The structure of the gas sensor element 10e is similar to that of the gas sensor element 10 of FIG. 1 in that the solid electrolyte body 100 is embedded in the insulating ceramic base 200 with the measuring electrode 110 and the reference electrode 120 affixed to opposed major surfaces thereof and wrapped around the cylindrical ceramic base 13, but different in that the heating element 140e is disposed on the surface of the insulating ceramic base 200 which is on the same side as the measuring electrode 110, and the insulating layers 192e and 193e are printed over the heating element 140d as protective layers which isolate the heating element 140d from the measurement gas. The insulating layers 192e and 193e are formed by the doctor blade techniques to have a thickness of 220 µm. The quick thermal activation of the solid electrolyte body 100 is, therefore, thought of as being achieved by shortening the insulating interval between the measuring electrode 110 and the heating element 140e. Additionally, the insulating layers 192e and 193e are thicker than the insulating layers 192d and 193 in the comparative example No. 5, thus minimizing the risk of deterioration of operation of the heating element 140d due to exposure to poisons in the measurement gas, as having penetrate pinholes in the insulating layers 192e and 193e. However, the heating element 140d is, like in the comparative example Nos. 2 and 5, located close to the outer periphery of the gas sensor element 10e, so that lots of thermal energy produced by the heating element 140e diffuses to the measurement gas around the gas sensor element 10e, thus resulting in lack of the thermal energy to heat the air in the reference gas chamber 130.

The increased thickness of the insulating layers 192e and 193e, however, undesirably absorbs the thermal energy produced by the heating element 140e, thus resulting in a delay in activating the gas sensor element 10e.

Figure 14A:
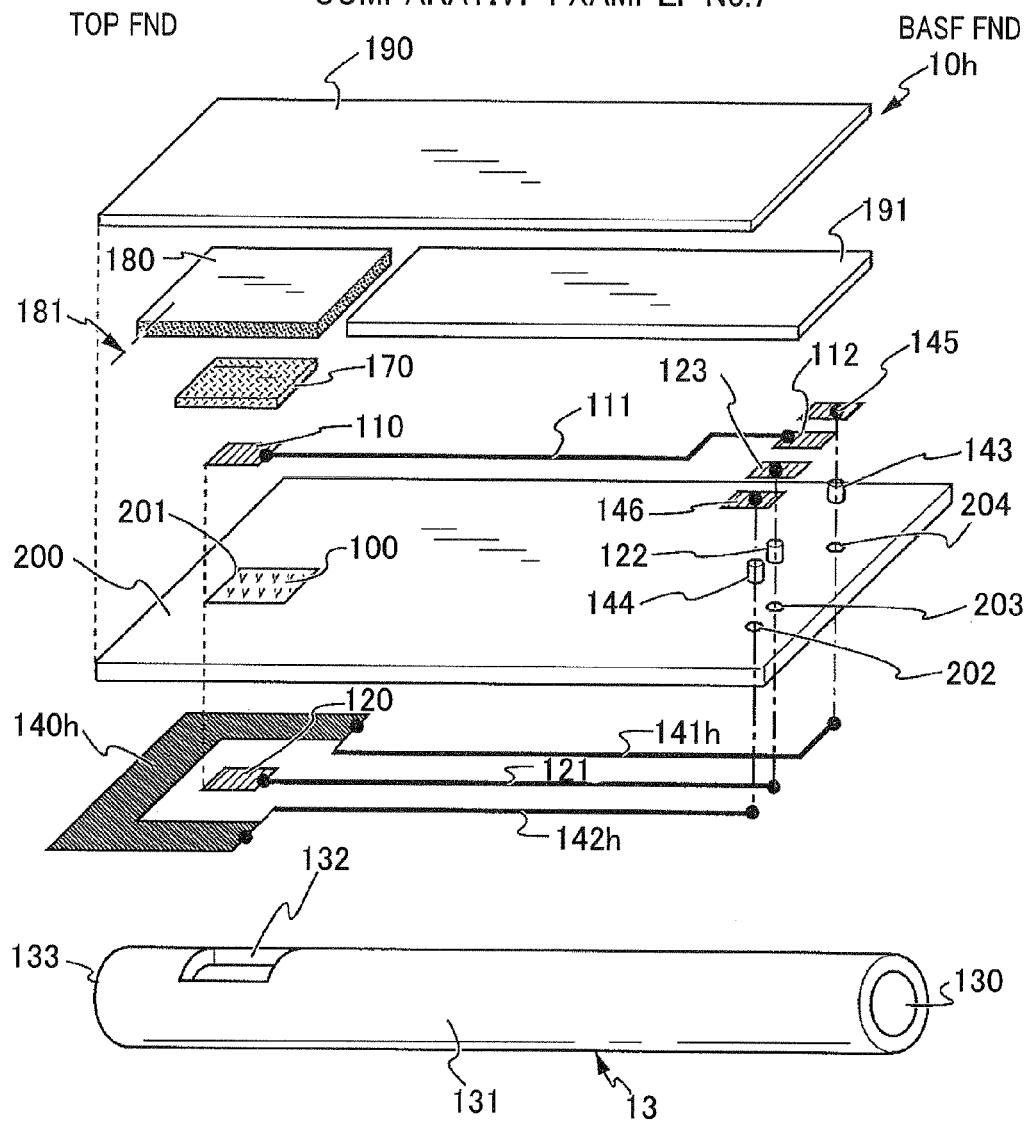
FIG. 14(a) is an exploded perspective view which shows a comparative example No. 7 of a gas sensor element.
Figure 14B:
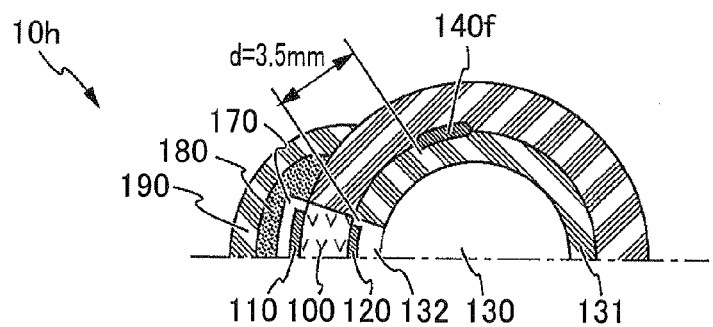
FIG. 14(b) is a partially transverse sectional view of the gas sensor element of FIG. 14(a).

FIGS. 14(a), 14(b), and 14(c) illustrate, as a comparative example No 7, the gas sensor element 10h. In FIGS. 14(a) to 14(c), the same reference numbers with or without a suffix "h", as those employed above, refer to similar or same parts, and explanation thereof in detail will be omitted here.

The gas sensor element 10h is different from the gas sensor element 10 of FIGS. 1(a) to 1(c) only in that the insulating interval d between the edge of the solid electrolyte body 100 and the heating element 140h is 3.5 mm which is greater than an upper limit of the set range of the insulating interval d in the gas sensor element 10 by 0.5 mm.

The increased insulating interval d results in an increase in time required to activate the gas sensor element 10h completely.

We performed tests, as discussed below, to evaluate the beneficial effects, as offered by the structure of the gas sensor element 10.

We prepared test samples identical in structure with the gas sensor element 10 and the comparative example Nos. 1 to 6 (i.e., the gas sensor elements 10z, 10g, 10f, 10c, 10d, and 10e and analyzed three test items: 1) activation time that is the time required to activate the test samples, 2) heater durability, and 3) thermal stress breakage.

Activation Time

We applied 6.5V to the heating element of each test sample, also applied 0.4V between the measuring electrode and the reference electrode, and measured the time that elapsed before a value of resulting current flowing through the measuring and reference electrode falls within ±2% of a constant or steady current. We found that less than 6 seconds is acceptable.

Heater Durability

We applied 6.5V to the heating element for 1,000 hours and then measured a change in resistance of the heating element. We determined that the heating element whose resistance didn't change is acceptable.

Thermal Stress Breakage

We energized the heating element and applied drops of water to each test sample. We measured a total volume of water applied until the test sample was broken. We defined such a total volume of water applied to the test sample of the comparative example No. 1 (i.e., the gas sensor element 10z) as a reference volume unit 10 and calculated the total volume of water applied to each test sample relative to the reference volume unit 10. Note that the higher the mechanical strength of each test sample, the more the total volume of water will be.

We shows results of the above tests in TABLE 1, as appears on the following page.

We found that, for the test sample of the gas sensor element 10 of the embodiment, the activation time was four seconds, the value of the resistance of the heating element was 1.9Ω either before or after the 1000 hour-durability test, and the applied total volume of water is much smaller than the reference unit 10. It is, thus, found that the gas sensor element 10 is substantially identical in degree of the heater durability with the comparative example No. 1, but excellent in the activation time and resistance to the thermal stress breakage. We gave a good overall rating "○" for the gas sensor element 10 in TABLE 1.

Comparative Example No. 1

The activation time of the comparative example No. 1 (i.e., the gas sensor element 10z) was ten seconds. However, we evaluated that an activation time of less than 10 seconds was required for being acceptable. The value of the resistance of the heating element was 2.0Ω either before or after the 1000 hour-durability test, Comparative Example No. 2

The activation time of the comparative example No. 2 (i.e., the gas sensor element 10g) was six seconds which is less than that of the comparative example No. 1, but longer than that of the gas sensor element 10. The value of the resistance of the heating element was 1.9Ω and 2.0Ω before and after the 1000 hour-durability test, respectively, which are almost identical with those of the gas sensor element 10. The applied total volume of water is smaller than that of the gas sensor element 10 even though the outer diameter is greater than that of the gas sensor element 10. This is because the heating element is located closer to the outer surface of the gas sensor element 10g, so that the temperature of the outer surface is elevated, thus resulting in an increase in thermal stress acting the surface of the gas sensor element 10g when splashed with water. We found that the activation time of the comparative example No. 2 is improved compared to the previous comparative example, but the resistance to the thermal stress breakage is lower than that of the comparative example No. 1 and thus gave a bad overall rating "x" for it in TABLE 1.

Comparative Example No. 3

The activation time of the comparative example No. 3 (i.e., the gas sensor element 10f) was four seconds which is approximately the same as the gas sensor element 10. The value of the resistance of the heating element was 1.9Ω and 2.0Ω before and after the 1000 hour-durability test, respectively, which are almost identical with those of the gas sensor element 10. The applied total volume of water is approximately half that of the comparative example No. 1. This is because the gas sensor element 10f is planar and wide and thus low in resistance to the thermal stress.

We found that the activation time of the comparative example No. 3 is greatly improved compared to comparative example No. 1, but the resistance to the thermal stress breakage is much lower than that of the comparative example No. 1 and thus gave a bad overall rating "x" for it in TABLE 1.

Comparative Example No. 4

The activation time of the comparative example No. 4 (i.e., the gas sensor element 10c) was four seconds which is approximately the same as the gas sensor element 10, but we observed the leakage of current from the heating element in the form of a significant electrical noise. The current output was not kept in ±2% of the steady current. The value of the resistance of the heating element was 1.9Ω either before or after the 1000 hour-durability test. The applied total volume of water is approximately the same as that of the gas sensor element 10.

We found that the activation time and the resistance to the thermal stress breakage are greatly improved, but the noise is great, and the reliability in operation of the gas sensor element 10c is not acceptable. We therefore gave a bad overall rating "x" for it in TABLE 1.

Comparative Example No. 5

The activation time of the comparative example No. 5 (i.e., the gas sensor element 10d) was four seconds which is approximately the same as that of the gas sensor element 10, but the value of the resistance of the heating element changed greatly from 2.0Ω to 28Ω after the 1000 hour-durability test. This is because the protective layers 192d and 193d are thin, which accelerates the deterioration of the heating element 140d. The resistance to the thermal stress breakage was approximately the same as that of the gas sensor element 10.

We found that the activation time and the resistance to the thermal stress breakage of the comparative example No. 5 are greatly improved, but the heater durability is low, and thus gave a bad overall rating "x" for it in TABLE 1.

Comparative Example No. 6

The activation time of the comparative example No. 6 (i.e., the gas sensor element 10e) was six seconds which is longer than that of the gas sensor element 10. This is because the heating element 140e is located closer to the outer surface of the gas sensor element 10e, so that the thermal energy produced by the heating element 140e is absorbed by the protective layers 192e 193d. The value of the resistance of the heating element was 1.9Ω and 2.0Ω before and after the 1000 hour-durability test, respectively, which are almost identical with those of the gas sensor element 10. The resistance to the thermal stress breakage was approximately the same as that of the gas sensor element 10.

We found that, for the comparative example No. 6, the resistance to the thermal stress breakage is greatly increased, the activation time is slightly improved, and the heater durability is acceptable and thus gave an average overall rating "Δ" for it in TABLE 1.

Comparative Example No. 7

The activation time of the comparative example No. 7 (i.e., the gas sensor element 10h) was six seconds which is longer than that of the gas sensor element 10. This is because the heating element 140h is located far away from the solid electrolyte body.

The gas sensor element 10h is cylindrical in shape. A slight increase in insulating interval d, thus, results in an increase in volume of a portion of the gas sensor element 10h through which the thermal energy produced by the heating element 140h is transmitted to the solid electrolyte body 100. Such a volume increase is thought of as contributing to the increase in the activation time.

The value of the resistance of the heating element was 1.9Ω and 2.0Ω before and after the 1000 hour-durability test, respectively, which are almost identical with those of the gas sensor element 10. The resistance to the thermal stress breakage was approximately the same as that of the gas sensor element 10.

We found that, for the comparative example No. 7, the resistance to the thermal stress breakage is greatly increased compared with comparative example No. 1, the activation time is slightly improved, and the heater durability is acceptable and thus gave an average overall rating "Δ" for it in TABLE 1.

As apparent from the above discussion, the gas sensor element 10 of the embodiment is made up of the cylindrical ceramic base 13 and the sensor/heater laminate sheet 20 stacked on the cylindrical ceramic base 13. The sensor/heater laminate sheet 20 has the solid electrolyte body 100 disposed in the insulating ceramic base 200. The solid electrolyte body 100 works to conduct at least a given ion (e.g., an oxygen ion) of gas. The cylindrical ceramic base 13 has the open end 134 (i.e., the inlet for the air) and the closed end 133. The cylindrical ceramic base 13 defines therein the reference gas chamber 130 and has formed therein the window 132 to which the reference electrode 120 affixed to one of the major surfaces of the solid electrolyte body 100 is exposed. The measuring electrode 110 is affixed to the other major surface of the solid electrolyte body 100 and exposed to the measuring gas. The heating element 140 is disposed on the surface of the insulating ceramic base 200 on the same side as that of the solid electrolyte body 100 on which the reference electrode 120 is mounted. The heating element 140 works to activate the solid electrolyte body 100 to produce a signal as a function of the concentration of a given component of the measurement gas.

The heating element 140 is located near the longitudinal center of the gas sensor element 10. This achieves quick activation of the gas sensor element 10 and ensures a required degree of durability thereof. The insulating interval d is, as described above, the shorter of a minimum distance between the inner edge of the heating element 140 and the outer edge of the reference electrode 120 and a minimum distance between the inner edge of the heating element 140 and the outer edge of the solid electrolyte body 100 and selected to be longer than or equal to 0.1 mm and shorter than or equal to 3 mm.

TABLE 1

| ACTIVATION TIME | RESISTANCE CHANGE | APPLIED WATER | RATING |
|---|---|---|---|
| Embodiment | 4 | 0.0Ω | 41 | ○ |
| Comparative Example No. 1 | 10 | 0.0Ω | 10 | X |
| Comparative Example No. 2 | 6 | 0.1Ω | 17 | X |
| Comparative Example No. 3 | 4 | −0.1Ω | 6 | X |
| Comparative Example No. 4 | 4 | 0.0Ω | 40 | X |
| Comparative Example No. 5 | 4 | 26.0Ω | 39 | X |
| Comparative Example No. 6 | 6 | −0.1Ω | 37 | Δ |
| Comparative Example No. 7 | 6 | 0.1Ω | 37 | Δ |

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor element which is sensitive to a given component of a gas comprising:
    a cylindrical insulating ceramic member which has surfaces opposed to each other and a through hole formed therein;
    a solid electrolyte body which is disposed in the through hole of the cylindrical insulating ceramic member and works to conduct at least a given ion, the solid electrolyte body having a first major surface and a second major surface;
    a measuring electrode disposed on the first major surface of the solid electrolyte body to be exposed to the gas;
    a reference electrode disposed on the second major surface of the solid electrolyte body to be exposed to a reference gas;
    a heating element disposed on one of the opposed surfaces of the cylindrical insulating ceramic member on a same side as the second major surface of the solid electrolyte body in a radial direction of the cylindrical insulating ceramic member, the heating element working to activate the solid electrolyte body; and
    a hollow cylindrical ceramic member which has a closed end and defines therein a reference gas chamber into which the reference gas is admitted, the hollow cylindrical ceramic member also having formed in a peripheral surface thereof a window which communicates with the reference gas chamber, wherein the cylindrical insulating ceramic member is stacked on the hollow cylindrical ceramic member with the solid electrolyte body exposed to the reference gas chamber through the window, and wherein the heating member is interposed between the hollow cylindrical ceramic member and the cylindrical insulating ceramic member.

2. A gas sensor element as set forth in claim 1, wherein the heating element is located at a given insulating interval away from one of the solid electrolyte body and the reference electrode, the insulating interval being a shorter one of a minimum distance between a peripheral edge of the heating element and a peripheral edge of the solid electrolyte body and a minimum distance between the peripheral edge of the heating element and a peripheral edge of the reference electrode and greater than or equal to 0.1 mm and smaller than or equal to 3 mm.

3. A gas sensor element as set forth in claim 1, wherein the solid electrolyte body is made of a partially-stabilized zirconia.

4. A gas sensor element as set forth in claim 1, wherein the insulating ceramic member is made of alumina.

5. A gas sensor which works to measure a given component of gas comprising:
    a gas sensor element including (a) an insulating ceramic member which has surfaces opposed to each other and a through hole formed therein, (b) a solid electrolyte body which is disposed in the hole of the insulating ceramic member and works to conduct to at least a given ion, the solid electrolyte body having a first major surface and a second major surface, (c) a measuring electrode disposed on the first major surface of the solid electrolyte body to be exposed to the gas, (d) a reference electrode disposed on the second major surface of the solid electrolyte body to be exposed to a reference gas, and (e) a heating element disposed on one of the opposed surfaces of the insulating ceramic member on the same side as the second major surface of the solid electrolyte body, the heating element working to activate the solid electrolyte body;
    a first and a second signal line leading to the reference electrode and the measuring electrode, respectively, for transmitting a sensor output to an external detection circuit;
    a first and a second conductor leading to the heating element for establishing electric connections with an external power supply control circuit to control supply of electric power to the heating element; and
    a housing in which the gas sensor element, the first and second signal line, and the power supply conductors are retained, the housing being designed to hold the gas sensor element to be exposed to the gas.

* * * * *